(12) United States Patent
Larson

(10) Patent No.: US 10,126,220 B2
(45) Date of Patent: Nov. 13, 2018

(54) SYSTEMS AND METHODS FOR DETERMINING SPECIFIC GRAVITY AND MINEROLOGICAL PROPERTIES OF A PARTICLE

(71) Applicant: National Oilwell Varco, LP., Houston, TX (US)

(72) Inventor: Thomas Robert Larson, Montgomery, TX (US)

(73) Assignee: National Oilwell Varco, L.P., Houston, TX (US)

( * ) Notice: Subject to any disclaimer, the term of this patent is extended or adjusted under 35 U.S.C. 154(b) by 753 days.

(21) Appl. No.: 14/333,604

(22) Filed: Jul. 17, 2014

(65) Prior Publication Data

US 2015/0020588 A1    Jan. 22, 2015

Related U.S. Application Data

(60) Provisional application No. 61/856,903, filed on Jul. 22, 2013.

(51) Int. Cl.
*G01N 15/02* (2006.01)
*G01N 9/00* (2006.01)
(Continued)

(52) U.S. Cl.
CPC .............. *G01N 9/00* (2013.01); *G01N 9/10* (2013.01); *G01N 9/34* (2013.01); *G01N 15/0205* (2013.01);
(Continued)

(58) Field of Classification Search
CPC .................. G01N 15/10; G01N 15/0211
(Continued)

(56) References Cited

U.S. PATENT DOCUMENTS

| 4,198,860 A | * | 4/1980 | King | ...................... G01F 1/363 222/55 |
| 5,376,280 A | * | 12/1994 | Wilhelm | ................ B01D 21/01 210/143 |

(Continued)

FOREIGN PATENT DOCUMENTS

| EP | 0289200 A2 | 11/1988 |
| EP | 0394316 B1 | 1/1996 |

(Continued)

OTHER PUBLICATIONS

Hoskins et al. "Kinetics analysis of binding between melanoma cells and neutrophils." Molecular & cellular biomechanics: MCB3.2 (2006): 79.*

(Continued)

*Primary Examiner* — Walter L Lindsay, Jr.
*Assistant Examiner* — Philip Marcus T Fadul
(74) *Attorney, Agent, or Firm* — Amerson Law Firm, PLLC

(57) ABSTRACT

A system includes a particulate material sample that contains a fluid medium and a plurality of particles dispersed in the fluid medium. The system further includes a particle analysis apparatus having a sample cell and sample delivery means for delivering the particulate material sample to the sample cell, wherein the particle analysis apparatus is adapted to obtain particle information on at least one particle in that particulate material sample while the at least one particle is in the sample cell. Furthermore, the system also includes fluid manipulation means for manipulating movement of the fluid medium while the particle analysis apparatus is obtaining the particle information on the at least one particle, and a data processing apparatus that is adapted to determine a specific gravity of the at least one particle based on the obtained particle information.

25 Claims, 11 Drawing Sheets

(51) Int. Cl.
  *G01N 15/10* (2006.01)
  *G01N 9/10* (2006.01)
  *G01N 9/34* (2006.01)

(52) U.S. Cl.
  CPC ......... *G01N 15/0211* (2013.01); *G01N 15/10* (2013.01); *G01N 2015/1043* (2013.01); *G01N 2015/1075* (2013.01)

(58) Field of Classification Search
  USPC ........................................................ 73/32 R
  See application file for complete search history.

(56) References Cited

U.S. PATENT DOCUMENTS

| | | | |
|---|---|---|---|
| 6,417,920 | B1 | 7/2002 | Shimaoka |
| 6,653,651 | B1 | 11/2003 | Meinhart et al. |
| 8,427,642 | B2 | 4/2013 | Mitchell et al. |
| 2009/0044608 | A1* | 2/2009 | Babcock .................. G01N 5/00 73/64.53 |
| 2010/0231909 | A1* | 9/2010 | Trainer .................. G01B 11/08 356/336 |
| 2011/0134426 | A1* | 6/2011 | Kaduchak .......... G01N 15/1404 356/337 |
| 2012/0301903 | A1* | 11/2012 | Putnam .................. G01N 21/05 435/7.92 |

FOREIGN PATENT DOCUMENTS

| | | |
|---|---|---|
| EP | 0644416 B1 | 12/1999 |
| EP | 2077330 A1 * | 7/2009 |
| JP | S59 159049 A | 9/1984 |

OTHER PUBLICATIONS

PCT International Search Report and Written Opinion dated Nov. 11, 2014 for international application No. PCT/US/2014/047185.
Gerald Houghton, Particle Trajectories and Terminal Velocities in Vertically Oscillating Fluids, The Canadian Journal of Chemical Engineering, Apr. 1, 1966, pp. 90-95.
Dynamic Liquid Image Analysis webpage, Particle Sizing Systems.
A Basic Guide to Particle Characterization, Inform White Paper, Malvern Instruments Worldwide, 2012.
Halliburton Brochure, Baroid Fluid Services, Baroid Surface Solutions, Baroid 1458 Centrigure—The Ultimate in Decanter Centrifuge System Design, Feb. 2008.
Laser Diffraction webpage, Particle Sizing Systems.
Light Obscuration webpage, Particle Sizing Systems.
Measuring instruments for particle size and fall velocity webpages, 1986.
Particle Size Analysis presentation.
Pirard, "3D Imaging of Individual Particles: A Review," Image Anal. Stereol., 31:65-77, 2012.
A Guidebook to Particle Size Analysis, Horiba Scientific, 2012.
Skalle, Drilling Fluid Engineering, 2011.
Stokes law, webpages from Wikipedia, Jun. 2013.

* cited by examiner

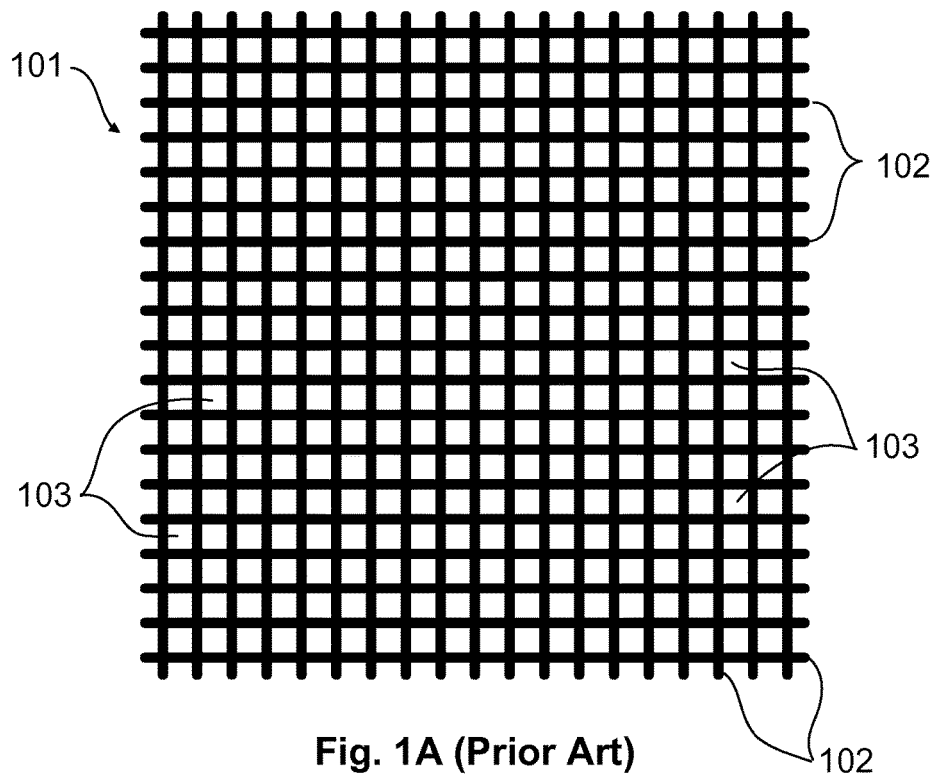
Fig. 1A (Prior Art)
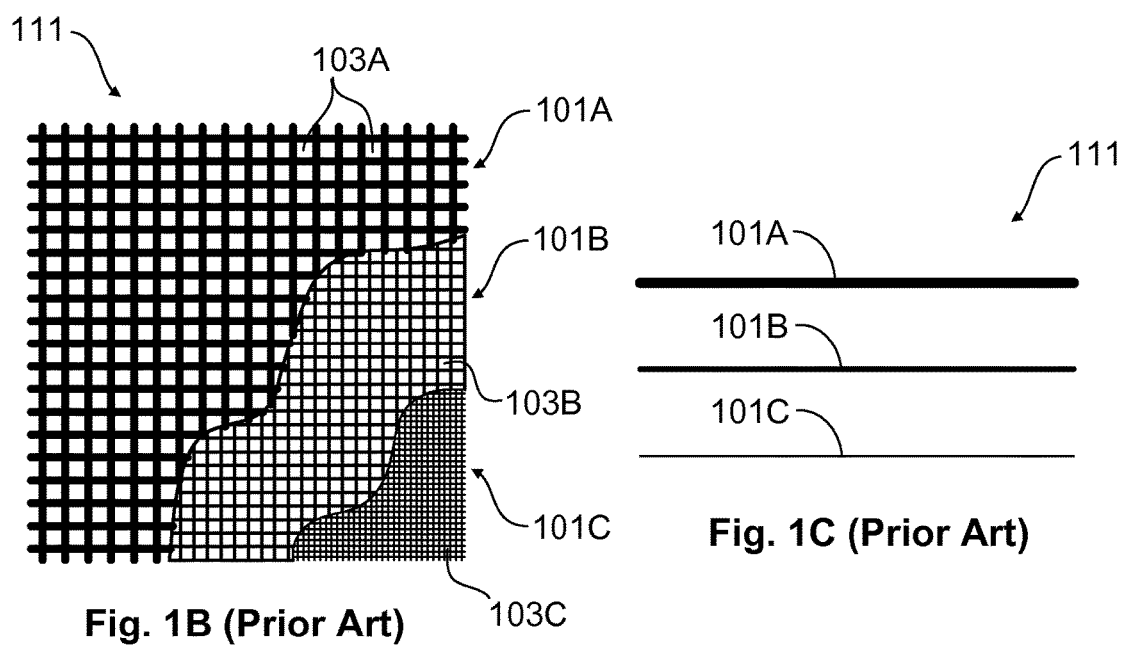
Fig. 1B (Prior Art)
Fig. 1C (Prior Art)

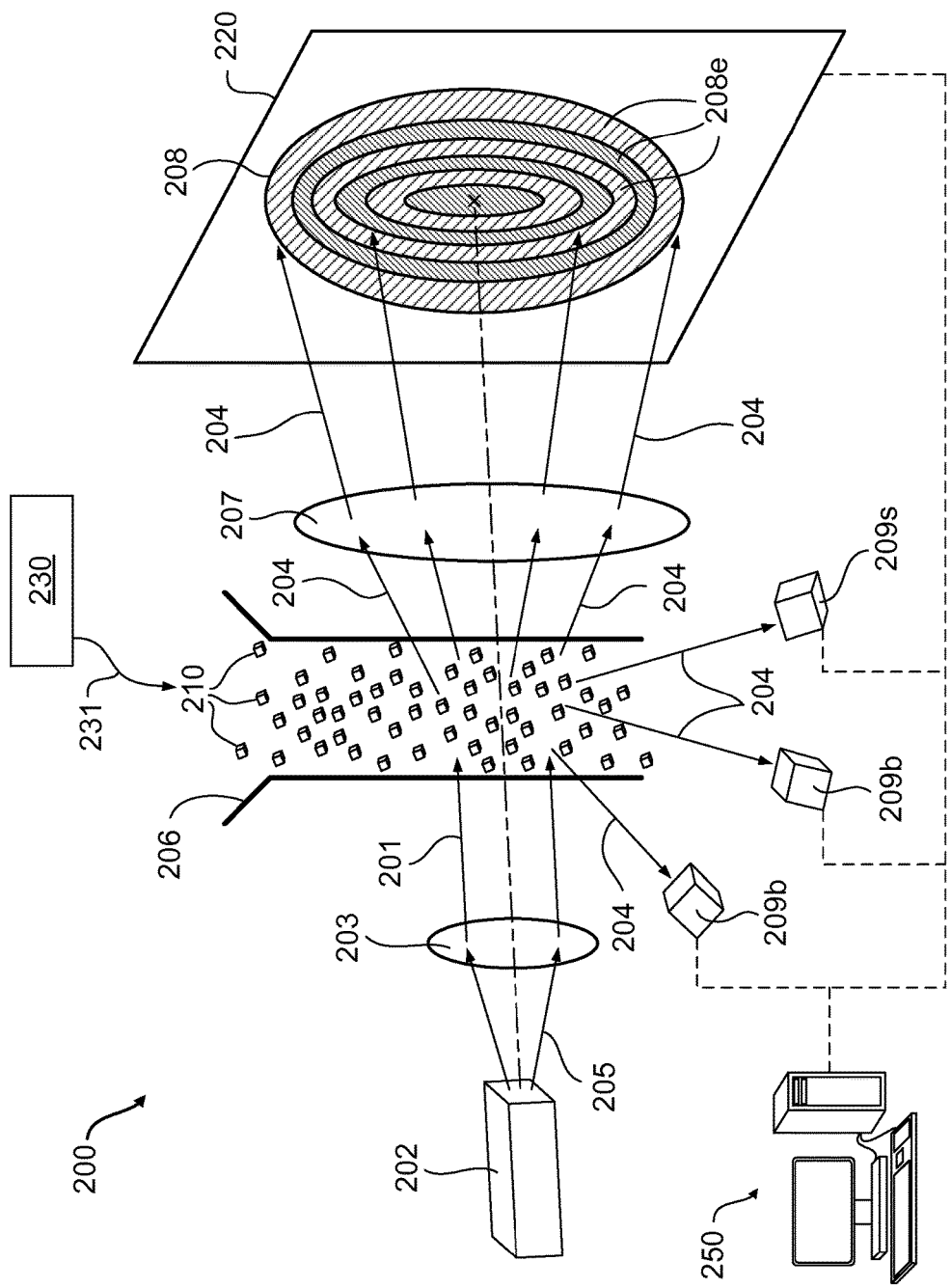

SYSTEMS AND METHODS FOR DETERMINING SPECIFIC GRAVITY AND MINEROLOGICAL PROPERTIES OF A PARTICLE

BACKGROUND

1. Field of the Disclosure

The present subject matter is generally directed to particle analysis, and in particular, to systems and methods that may be used for determining the specific gravity and minerological properties of solids particles.

2. Description of the Related Art

Many different industries rely on an accurate assessment of the physical properties of particles in order to provide particulate materials, such as powders, suspensions, emulsions, and the like, that can meet a variety of different quality and/or performance characteristics. For example, particle size and shape can greatly influence the flow and/or compaction properties of powders, where larger, more spherically shaped particles will flow more easily than smaller and/or irregularly shaped particles having significant aspect ratios. Furthermore, smaller particles often lead to higher suspension viscosities and an improvement in suspension and/or emulsion stability. Accordingly, significant efforts are employed to determine the shape and measure the size of the particles that are used in and/or created during various processing operations by utilizing a variety of different laboratory techniques.

Following is a brief description of some representative types of prior art devices and techniques that are commonly used to determine particle shape and/or size. It should be appreciated that this is not an exhaustive review of all prior art methods that may be employed or devices that may be used to perform particle size analysis, but is instead intended to simply provide some exemplary general background information on some aspects of the state of the art.

One of the simplest ways of determining the distribution of particle sizes that make up a given particulate material is by sieving, which typically utilizes a woven screen or mesh to separate the various particles by their respective sizes. In general, sieving involves introducing a particulate material sample to the surface of a screen, such as the screen 101 that is shown in top, or plan view, in FIG. 1A. The screen 101 is generally made up of a plurality of crisscrossing wires 102, the size (i.e., diameter or width) and spacing of which define an aperture 103, or open space, between the crisscrossing wires 102. The number of wires over a given linear distance (such as inches) define what is often referred to as a mesh size, or sieve number. During a sieving operation, the screen 101 is shaken or vibrated so that particles which have a size that is smaller than the aperture 103 pass through the screen 101, whereas larger particles remain trapped above the screen 101 by the crisscrossing wires 102.

In many sieving operations, a plurality of stacked screens may be used to separate multiple different particle sizes. For example, FIG. 1B is a partial cutaway top, or plan view, of a screen stack 111 that includes screens 101a/b/c, and FIG. 1C is a side, or elevation view, of the stack 111 shown in FIG. 1B. In a typical multiple screen sieving operation, each of the screens 101a/b/c of the screen stack 111 will have a smaller sized respective aperture 103a/b/c (e.g., a higher mesh number) than the screen immediately thereabove. Therefore, as the particulate matter travels sequentially from the top of the stack 111—where the screen 101a with the largest aperture size 103a is positioned—to the bottom of the stack 111—where the screen 101c with the smallest aperture size 103c is positioned—progressively smaller particles will be trapped on each screen, while only the finest particles pass through the lowermost (highest mesh number) screen 103c. Of course, it should be appreciated the number of screens shown in FIGS. 1B and 1C is illustrative only, as more or fewer screens may be used in the screen stack 111, depending on the targeted basis for the sieving operation. Data that is based on the amount, e.g., weight percent, of each of the different sized particles making up the particulate material sample in question can then be gathered and assessed in order to determine whether the sample meets the requisite quality and or performance standards.

Sieving has some inherent shortcomings that can be problematic when different types of particles and/or materials are mixed together in the same particulate material sample. More specifically, in mixed samples, it is quite often the case that the particles which are able to fit through the aperture of a given screen do not necessarily have the same overall size and shape. For example, particles which have an approximately spherical shape of a given diameter would pass through the same sized screen aperture as an elongated or rod-shaped particle which may have maximum projected sizes/widths in two dimensions that are substantially the same as (or smaller than) that of the spherically shaped particle, but may also have a size/length in the third dimension that is substantially greater than that of the spherically shaped particle. In certain cases, when the screens are vibrated or shaken, particles will have a certain probability of aligning themselves in such a manner as to allow the minimum particle dimensions, such as width or diameter, to pass through the aperture in the screen. Accordingly, particles having completely different shapes and/or volumes may end up together in the same "separated" portion of a sample, simply because they have at least two dimensions in common. In such cases, the particle shape—not its minimum nor maximum dimension (or size)—may become a driving factor in proper particle separation.

Another method of determining particle size that has also been in common use for many years is a laser diffraction technique. FIG. 2 schematically depicts an illustrative prior art laser diffraction particle size analyzing apparatus 200 that may be utilized for this purpose. Generally, when using the laser diffraction technique, the size distribution of a plurality of particles 210 can be calculated by measuring a space intensity distribution of the diffracted/scattered light 204 that is generated when the particles 210 are irradiated with one or more laser beams 201 (one shown in FIG. 2) from one or more laser light sources 202 (one shown in FIG. 2) while the particles 210 are in a substantially dispersed or separated state. Thereafter, data from the diffracted/scattered light 204 may be used to calculate particle sizes based on light scattering and diffraction theories that are well known in the art.

During operation of the illustrative laser diffraction apparatus 200 shown in FIG. 2, a particulate material sample 231 containing the particles 210 is directed from a sample source 230 to a sample cell 206 so that data on the particles 210 can be obtained. Light 205 from a laser light source 202 is used to irradiate the group of particles 210 by passing the light 205 through a collimating lens 203, which is used to focus the light 205 into a parallel laser beam 201. The laser beam 201 is then diffracted or scattered by the particles 210 as they pass through the sample cell 206 so as to thereby form a spatial light intensity distribution pattern. The forward diffracted/scattered light 204 is converged by a lens 207 to form ring-shape diffracted/scattered images on a detection plane 220 disposed at a focal distance position. The intensity distribution pattern of the forward diffracted/scattered light 204 is detected by a ring detector (forward diffracted/scattered light sensor) 208 formed from a plurality of light sensor elements 208$e$ having ring-shape light receiving surfaces of different radii that are arranged concentrically on the detection plane 220. The sideward diffracted/scattered light 204 is detected by sideward diffracted/scattered light sensors 209$s$ and the backward diffracted/scattered light 204 is detected by backward diffracted/scattered light sensors 209$b$. Thereafter, the space intensity distribution pattern of the diffracted/scattered light 204 that is measured by each of the various plurality of light sensors 208$e$, 209$s$, 209$b$ is digitized by an analog/digital converter apparatus (not shown) and input to data processing apparatus 250, such as a computer with suitable analysis software and the like, as the diffracted/scattered light intensity distribution data. Particle size and particle size distribution information can then be calculated with the data processing apparatus 250 as previously noted, i.e., based upon the diffracted/scattered light intensity distribution data, from which quality and performance assessments of the particulate material sample can then be made.

As with sieving, the laser diffraction measurement technique may also present some problems associated with particle shape. This is because laser diffraction does not directly evaluate a given particle size, but instead gathers information from the diffracted/scattered light intensity which is then used to indirectly calculate particle volumes. The algorithms that are typically used to calculate particle size based upon the diffracted/scattered light intensity distribution data thus provide information on particle size that is based on a theoretical equivalent spherical diameter, as the gathered data provides little, if any, information on shape. Therefore, when analyzing a particulate material sample containing a mixture of different types of particles made up of different materials and/or having substantially different shapes, the laser diffraction technique may not be able to distinguish between such varied particles.

Another technique for measuring particle size and size distribution that has been more recently developed is a digital optical imaging technique. FIG. 3 schematically illustrates an exemplary prior art digital optical imaging apparatus 300 that may be used for this purpose. Generally, when using the digital optical imaging technique, the size distribution of a plurality of particles 310 can be determined by obtaining a plurality of digital images of the particles 310 as they pass in front of a digital camera 302. In some aspects, the digital optical imaging technique is similar to the laser diffraction technique described above in that a particulate material sample 331 containing the particles 310 is typically directed from a sample source 330 to a sample cell 306 where they pass in front of the digital camera 302. As with the laser diffraction apparatus described above, the particles 310 are also generally in a substantially dispersed or separated state as so to avoid undue imaging interference between adjacent or nearby particles.

An optical magnification device 303, such as a lens system and the like, is typically used to magnify and focus the digital camera 302 on the particles 310 as they pass through the sample cell 306. In a typical digital optical imaging apparatus, the front-to-back width 306$w$ of the sample cell is usually narrow, as the depth-of-focus of the digital camera 302 is often limited, particularly when the optical magnification system 303 is operated under very high magnifications for viewing and imaging particles smaller than 200-300 μm (microns). As such, the width 306$w$ is often minimized so that most, if not all, of the particles 310 pass through the focal plane of the digital camera 302 and optical magnification device 303.

In some digital optical imaging systems, such as the apparatus 300 shown in FIG. 3, a light source 301 is positioned so the particles 310 to be measured and the sample cell 306 through which they pass are between the digital camera 302 and the light source 301. During operation of the apparatus 300, the light source 301 is operated so that a light beam 301$b$ from the light source 301 passes through the sample cell 306 and illuminates the particles 310 so that digital images can be captured by the digital camera 302. In many applications, the light source 301 is, for example, a strobe light, such as an LED strobe light and the like, which can be operated to flash up to several thousand times per second, thereby making it is possible to capture a large number of digital images of a single particle while that particle remains in the field of view 302$v$ of the digital camera 302. The various digital images obtained by the digital camera 302 may then be transmitted to an image processing system 350, such as a computer that uses a data analysis program, and the like, and the processed image data may then be used to calculate particle size and size distribution information on the particulate material sample.

In many applications, digital optical imaging systems are generally operated so as to obtain a 2-dimensional or "outline" image of particles. The size of particles in the third dimension are then assumed based upon typical particle configurations for the known types of particles that are being imaged. However, as noted above, when the light source 301 that is used during the imaging process is a high frequency strobe lighting apparatuses, some systems can be operated to obtain numerous images of the same particle while that particle remains within the field of view 302$v$ of the digital camera 302, as described above. With this capability in mind, some digital optical imaging systems have been adapted to impart a spin, or rotational motion, to the particles 310 prior to passing them through the field of view 302$v$. Digital optical imaging apparatuses that are modified in this way are therefore able to gather more than just routine 2-dimensional image data of a given single particle. Instead, by obtaining numerous sequential 2-dimensional images of the same individual particle as it spins and passes through the field of view 302$v$, a properly designed data analysis program may enable the image processing system 350 to construct a 3-dimensional image of the particle. In this way, some digital optical imaging systems may theoretically be able to provide more accurate data as to the actual shape of a given particle.

Each of the particle size analysis systems described above may be configured so as to operate as a "dry" system or as a "wet" system. "Dry" systems are those in which the particles to be measured flow through a substantially gaseous medium, such as air or an inert gas and the like. On the other hand, "wet" systems are those wherein the particles flow through and/or with a liquid, such as water, oil, alcohol, and/or mixtures of water or alcohol with other liquids. Liquids are often used as the flow medium when using the laser diffraction or digital optical imaging techniques, as the higher viscosity liquids enable the particles to be diluted and properly dispersed so that accurate measurements and data gathering can be performed.

The various methods and apparatuses described above are generally used to obtain size and shape information about the particles that make up a particulate material sample. While, as previously noted, such information on the size and shape of particles can be helpful in many different applications, there is sometimes a need to obtain information regarding other physical and/or chemical properties of particles that may be beneficial in supporting and even improving certain industrial, manufacturing, or mining operations. The following disclosure is directed to new and unique methods and techniques of utilizing one or more of the particle size analysis apparatuses described above so as to obtain information about the properties of particles other than size and shape, and the systems in which such methods and techniques are implemented.

SUMMARY OF THE DISCLOSURE

The following presents a simplified summary of the present disclosure in order to provide a basic understanding of some aspects disclosed herein. This summary is not an exhaustive overview of the disclosure, nor is it intended to identify key or critical elements of the subject matter disclosed here. Its sole purpose is to present some concepts in a simplified form as a prelude to the more detailed description that is discussed later.

Generally, the subject matter disclosed herein is directed to various new and unique methods, techniques, and systems that may be used to obtain useful information on the properties of various particles that make up a particulate material sample, such as, for example, specific gravity and the like.

In one illustrative embodiment, a system is disclosed that includes, among other things, a particulate material sample that contains a fluid medium and a plurality of particles dispersed in the fluid medium. The system further includes, among other things, a particle analysis apparatus having a sample cell and sample delivery means for delivering the particulate material sample to the sample cell, wherein the particle analysis apparatus is adapted to obtain particle information on at least one particle in that particulate material sample while the at least one particle is in the sample cell. Furthermore, the system also includes fluid manipulation means for manipulating movement of the fluid medium while the particle analysis apparatus is obtaining the particle information on the at least one particle, and a data processing apparatus that is adapted to determine a specific gravity of the at least one particle based on the obtained particle information.

In another embodiment, a method is disclosed that includes delivering a particulate material sample to a sample cell of a particle analysis apparatus, the particulate material sample containing a fluid medium and a plurality of particles dispersed in the fluid medium, at least some of the plurality of particles having different specific gravities. The method also includes obtaining particle information on the particulate material sample with the particle analysis apparatus while the plurality of particles are in the sample cell, analyzing the particle information with a data processing apparatus, and determining a first specific gravity of a first particle of the plurality of particles from the analyzed particle information. Additionally, the method includes, among other things, determining a second specific gravity of a second particle of the plurality of particles from the analyzed particle information, wherein the second specific gravity is different from the first specific gravity.

BRIEF DESCRIPTION OF THE DRAWINGS

The disclosure may be understood by reference to the following description taken in conjunction with the accompanying drawings, in which like reference numerals identify like elements, and in which:

FIG. 1A is a top or plan view of a typical prior art screen can be used separate and size particles during a sieving operation;

FIGS. 1B and 1C depict various views of an exemplary prior art screen stack that can be used for particle sizing and/or particle separation during a sieving operation;

FIG. 2 is a schematic view of an illustrative prior art laser diffraction apparatus that can be used for determining particle information;

Figure 3:
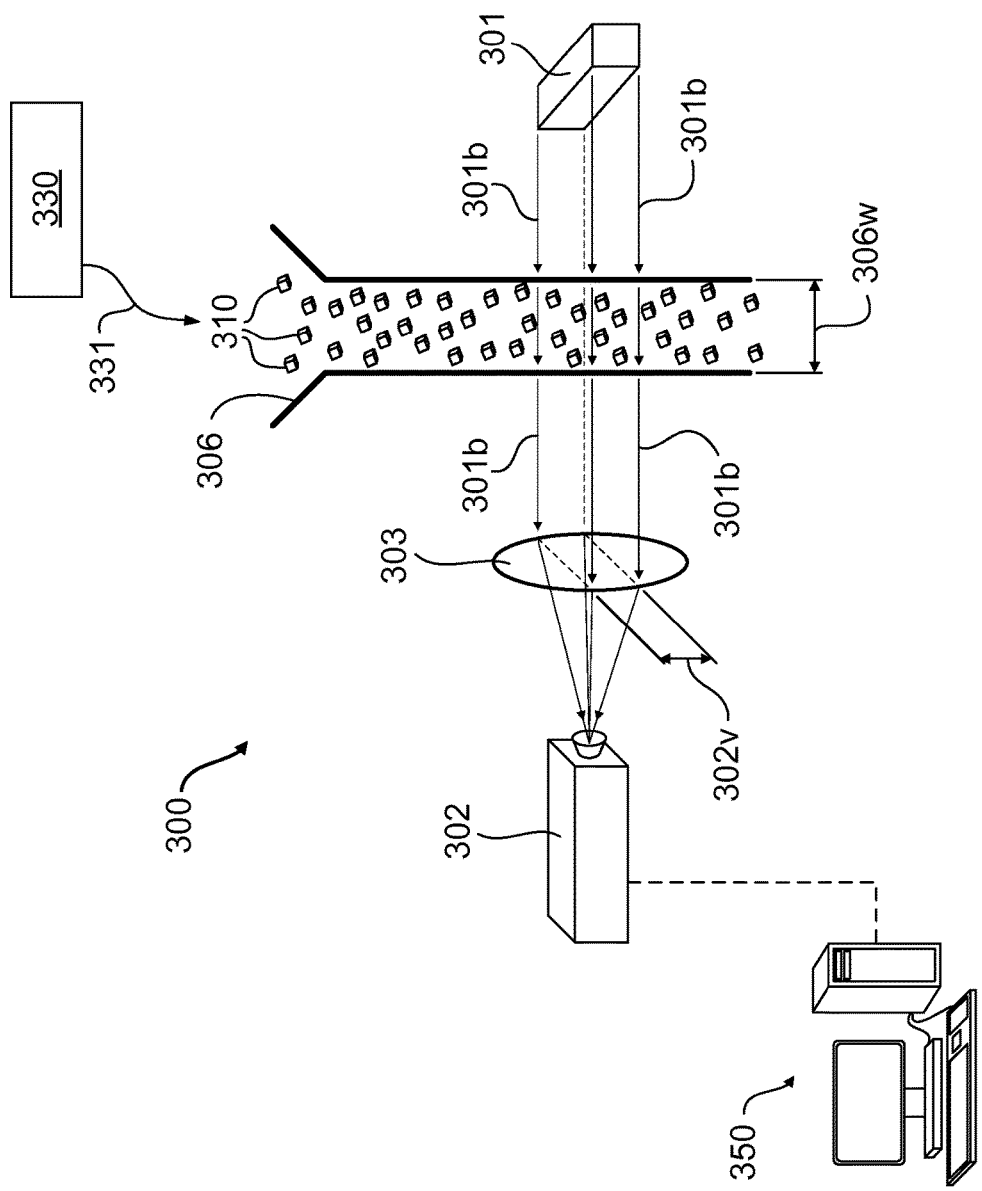
FIG. 3 is a schematic view of an exemplary prior art digital optical imaging apparatus that can be used for obtaining particle information.

While the subject matter disclosed herein is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention.

DETAILED DESCRIPTION

Various illustrative embodiments of the present subject matter are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present subject matter will now be described with reference to the attached figures. Various systems, structures and devices are schematically depicted in the drawings for purposes of explanation only and so as to not obscure the present disclosure with details that are well known to those skilled in the art. Nevertheless, the attached drawings are included to describe and explain illustrative examples of the present disclosure. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than that understood by skilled artisans, such a special definition will be expressly set forth in the specification in a definitional manner that directly and unequivocally provides the special definition for the term or phrase.

Generally, the present disclosure is directed to methods and systems that may be used to obtain useful information on the properties of the various particles that make up a particulate material sample. As noted above, there are a variety different machines and techniques available in the marketplace that may be used to analyze particles, but these commonly available machines are generally used for determining the size and/or shape of particles in a sample. In many cases, information on size and/or shape and size distribution can be particularly beneficial, depending on the specific application. However, the inventor has recognized there are other properties of particles that are equally important in many industrial applications—if not more so—yet the marketplace has failed to deliver pertinent systems and/or methodologies that can be used to determine many of these other properties.

In many solid particle separation systems, particle size may be only one of several important criteria that may be used to separate and remove undesirable materials from a given flow stream of mixed solids and/or mixed solids and liquids. For example, particle size may be one criteria that is used as a specifically targeted set point to determine the operational proficiency of a particle separation system, whereas, in certain types of systems, particle density may be an equally important criteria that is used to evaluate machine performance.

One such exemplary system is a drilling mud circulation and recovery system, which is generally used to circulate drilling fluid, i.e., drilling mud, into and out of a wellbore during a drilling operation, such as when drilling an oil and gas well into the earth. The drilling mud provides many functions and serves many useful purposes during the drilling operation, such as: removing drill cuttings from the well; suspending drill cuttings; controlling formation pressures during drilling; sealing permeable formations; maintaining wellbore stability; cooling, lubricating, and supporting the drill bit and drill assembly; transmitting hydraulic energy to the drilling tools and bit; ensuring adequate formation evaluation; controlling corrosion; facilitating well cementing and completion; and minimizing impacts on the environment. Drilling muds commonly include many different types of desirable solid particles that aid in performing one or more of the functions and purposes outlined above. These solids particles used in drilling muds may have one or more particular properties which makes their presence in a particular drilling mud mixture desirable and beneficial.

For example, some solids particles may need to be of a certain size or size range, which may be useful in sealing off more highly permeable formations so as to prevent the loss of valuable drilling fluid into the formation—so-called "lost circulation materials." Other solids particles may need to be of a certain density so as to control and balance forces within the wellbore, which may be added as necessary to the drilling mud so as to guard against wellbore collapse or a well blowout during the drilling operation. High density particulate materials such as barium sulfate, or barite, ($BaSO_4$), are often used for this purpose, as their greater unit volumetric weight serves to counterbalance high formation pressures and/or the mechanical forces caused by formations that would otherwise begin sloughing. In still other cases, solids particles may be added to the drilling mud based on a combination of the particle size and density, such as when a specific combination of the two properties may be desirable. Furthermore, the drilling mud in general, and the added solid particles in particular, can be very expensive. As such it is almost universally the case that upon circulation out of the wellbore, the desirable—and valuable—solids particles are generally recovered and re-used during the ongoing drilling cycle.

Once the drilling mud has served its initial purposes downhole, the mud is then circulated back up and out of the well so that it can carry the drill cuttings that are removed from the advancing wellbore during the drilling operation up to the surface. As may be appreciated, the drill cuttings, which are also solids particles, are thoroughly mixed together with the desirable solids particles that, together with various types of fluids, make up drilling mud, and therefore must be separated from the desirable solids particles, such as barite and the like. In the best possible drilling scenario, it is advantageous for most, if not all, of the drill cuttings to be substantially larger than the desirable solids particles making up the drilling mud. In such cases, the drill cuttings can be relatively easily removed using separator devices that separate particles based upon size, such as shale shakers, vibratory separators, and the like, which are designed to operate much like the screening/sieving technique described above.

For example, in accordance with API Specification 13A, barite that is added to drilling mud is required to be made up of particles having a particle size distribution wherein no more than 3 weight percent is coarser than 75 microns and no more than 30 weight percent is finer than 6 microns. Therefore, the majority of the barite particles that are used in drilling mud have a particle size that ranges from 6-75 microns, with the allowances outside of this range as noted above. Furthermore, the median particle size in this distribution range is typically on the order of around 50 microns. When using a shale shaker or other vibratory separator, better operational proficiency is achieved by the machines when the size of the drill cuttings particles are at least twice that of the valuable solids particles—e.g., barite—that are desirable to keep in the drilling mud mixture. Therefore, drill cuttings particles that are 150 microns or larger can generally be separated rather efficiently from particles such barite using well known and commonly available screen separation technology.

However, it should be appreciated that while the sizes of at least some of the drill cuttings particles enable them to be separated with machines that utilize screen/sieving techniques, such as shale shakers and the like, the sizes of other particles generally do not fall within the size range that permits such relatively easy separation, e.g., the 150 micron size threshold noted above. This is because there are many factors that influence the size of drill cuttings particles, such as: formation lithology (different rocks/minerals that are encountered as the wellbore progresses through different formation strata); type of drill bit used (PDC bits cut or shear rock; roller-cone bits crush rock); weight on bit (downward force exerted on the bit by gravity and/or mechanical forces); drilling rate (feet per hour), and the like. Accordingly, the sizes of drill cuttings particles may fall squarely within the size range of the drilling mud's desirable solids particles, such as the 6-75 micron size range of barite particles, as noted above.

There are a variety of reasons why it is desirable, and even necessary, to remove as many of the drill cuttings particles from the drilling mud mixture as possible. A first reason would be so as to control and/or maintain the drilling mud chemistry and composition within a desirable range as consistently as possible. For example, the presence of drill cuttings particles in the drilling mud mixture may have a significant effect on the weight of the mud, which could potentially lead to wellbore collapse, and/or a blowout scenario associated with possibly hazardous overpressure conditions within the well. More specifically, because the specific gravity of the drill cuttings particles (that is, the ratio of the drill cuttings particle density to that of water) are normally significantly lower than that of the desired solids particles in the drilling mud, e.g., barite, then the presence of cuttings particles left in the mud by the typical solids removal processes can cause the weight of the drilling mud to be lower than required when the cuttings particles displace the barite. Mineralogically pure barite, or barium sulfate, has a density of about 4.5 gm/cm$^3$ (or a specific gravity of 4.5), whereas the types of cuttings materials often encountered during drilling operations typically have a specific gravity that less than 3.2 and generally fall in the range of 2.5 to 3.0.

Additionally, the presence of undesirable solids materials in the drilling mud can also have an adverse effect on the flow and/or hydraulic characteristics of the mud, which could thus potentially detrimentally influence the operational efficiency of the hydraulically driven downhole tools, lubrication and cooling of the drill bit, and the like. Furthermore, depending on the types of materials (e.g., rocks/minerals) that make up the drill cuttings, the drill cuttings particles can be highly abrasive, and therefore could be damaging to the drilling mud circulation equipment, such as mud pumps, seals, valves, and the like. In such cases, expensive drilling downtime may be encountered during the repair and/or replacement of inordinately worn or damaged equipment. Accordingly, more sophisticated techniques are sometimes necessary in order to separate the undesirable drill cuttings particles from the drilling mud while leaving the desirable solids particles in the mud during the drilling mud recovery cycle, as will be further described below.

Figure 4:
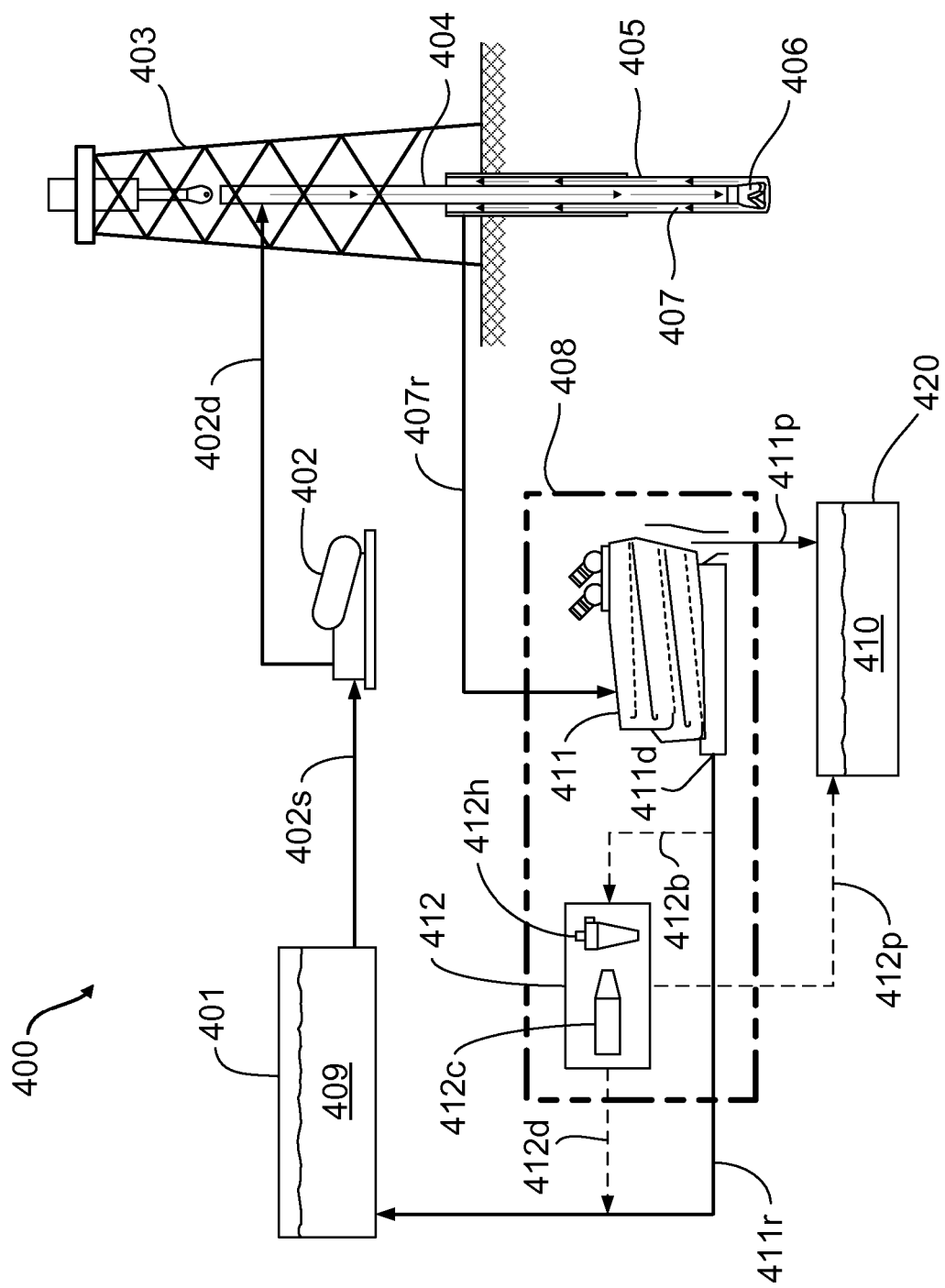
FIG. 4 schematically depicts an illustrative drilling mud circulation and recovery system.

FIG. 4 depicts a simplified schematic diagram of a mud circulation system 400 that may be used to circulate and recover drilling mud that is used during a wellbore drilling operation. As shown in FIG. 4, a mud pump 402 is used to pump drilling mud 409 from a mud tank 401 via the suction line 402s to a drill string 404 in a drilling rig 403 via the discharge line 402d. The drill string 404 extends down into wellbore 405 that is being drilled by a drill bit 406 at the bottom end of the drill string 404. The drilling mud 409 circulates down the drill string 404, where it is used to, among other things, cool and lubricate the drill bit 406, after which it is circulated back up the annulus 407 of the wellbore 405 to the surface. At this stage, drill cuttings 410 that are generated by the drilling operation are mixed with the drilling mud 409, and the mixed drilling materials, i.e., a mixture of drilling mud 409 and drill cuttings 410 is circulated to a separation system 408 via the wellbore annulus return line 407r. In a primary separation stage, the mixed drilling materials (i.e., the mixture of drilling mud 409 and drill cuttings 410) is sent via the return line 407r to a vibratory separator 411, such as a shale shaker, where at least a portion 411p of the undesirable drill cuttings 410 are removed from the mixed drilling materials and directed to a waste disposal pit 420.

In those cases where undesirable drill cuttings particles 410 are of such a size that the screening/sieving operation performed by the shale shaker 411 is able to remove most or substantially all of the drill cuttings 410 from the incoming mixed drilling materials, the effluent material exiting the shale shaker 411 at the shaker discharge 411d, which may be substantially made up of drilling mud 409, is then returned to the mud tank 401 via the mud return line 411r, where it is reconditioned for re-use. However, in those cases where most or substantially all of the undesirable drill cuttings particles 410 cannot be separated from the mixed drilling materials based upon size criteria alone—e.g., by operation of the shale shaker 411—the effluent material exiting the shale shaker 411 may be circulated to a secondary separation apparatus 412 via the bypass line 412b. As shown in FIG. 4, the secondary separation apparatus may include, for example, a hydrocyclone apparatus 412h, a centrifuge apparatus 412c, and/or both. The secondary separation apparatus is then operated so as to separate a further portion 412p of undesirable drill cuttings particles 410 from the mixed drilling materials entering the apparatus 412 via the bypass line 412b, which are also sent to the waste disposal pit 420. The effluent material exiting the secondary separation apparatus 412 is then sent via the discharge line 412d back to the mud tank 401.

Hydrocyclones and centrifuges both operate on principles that are related to Stokes' Law, which describes the drag force, i.e. frictional force, on a spherical particle in a continuous viscous fluid. In a hydrocyclone or centrifuge, a fluid containing both light and heavy components is spun at a high rotational velocity inside of a vessel (which in the case of a hydrocyclone is substantially conically shaped, and in the case of a centrifuge is substantially cylindrically shaped), thereby imparting a centripetal acceleration to the fluid. In the case of a hydrocyclone separator, the fluid is introduced at a high velocity tangentially to the inside surface of the conically shaped vessel, which causes the fluid to spin rapidly along the inside surface while the hydrocyclone remains fixed in place. In the case of a centrifuge separator, the cylindrical vessel is rotated at a very high angular velocity, and the fluid is introduced substantially along the central axis of the machine. The spinning centrifuge imparts a rotational velocity to the fluid, which is moved along the length of the centrifuge by interaction with a screw or scroll, which is inside of and rotates with the vessel, but at a slightly different angular velocity.

When the heavy components in the fluid are solids particles, such as mixed drilling materials discussed above, the centripetal acceleration of the fluid gives the particles a momentum that tends to move the particles outward toward the inside surface of the vessel wall. However, based on the principles of Stokes' Law, there is also a drag force working against the momentum of the particles, which consequently resists the movement of the particles toward the vessel wall. Therefore, the competing momentum and drag forces acting on a given particle will determine whether or not that particle will be able to be separated from the fluid, or whether it will remain entrained in the fluid as it flows out of the hydrocyclone/centrifuge. As such, particles having a great enough momentum to overcome the fluid drag force are able to move toward, and become "pinned" to, the inside of the vessel wall, whereas particles without sufficient momentum to overcome the fluid drag force will remain closer to the central axis of the machine. In the case of, for example, a hydrocyclone separator, the higher momentum/lower drag force particles that are "pinned" to the inside wall of the vessel will eventually move down the inside of the conical shell by gravity and/or due to internal pressure action and out the bottom of the hydrocyclone through the underflow outlet. On the other hand, the lower momentum/higher drag force particles that remain near the centerline of the hydrocyclone will remain entrained in carrier fluid, and they will be "dragged" from the machine by the carrier fluid as the fluid is forced out of the overflow outlet at the top of the hydrocyclone. Similar drag/momentum forces act to separate particles in a centrifuge apparatus.

As the foregoing discussion illustrates, secondary separation devices such as hydrocyclone and centrifuge apparatuses operate to separate particles based on a competing drag force vs. momentum basis. In this way, higher density solids particles of a given size—such as barite particles and the like—can be readily separated from lower density solids particles of the same given size—such as smaller (finer) drill cuttings particles. Therefore, for a given particle size or particle size range, these hydrocyclones and centrifuges are able, to some degree, to separate particles based on the density, or specific gravity, of the particles. However, it should be appreciated that, in certain circumstances, some larger (more coarse), low density (low specific gravity) drill cuttings particles may have sufficient momentum to overcome the drag force effect caused by the moving fluid inside of the machine, and become "pinned" to the inside surface of the separator vessel along with the desirable small (fine), high density (high specific gravity) particles, such as barite. As such, it is possible that many undesirable lower specific gravity coarse sized particles may inadvertently be separated together with the more desirable higher specific gravity fine sized particles, thereby detrimentally affecting the properties of the recovered drilling mud.

In such cases such as those described above, the operation of the secondary separation apparatus 412 can be controlled and/or adjusted so as to reduce the likelihood of low specific gravity coarse particle carryover into the recovered drilling mud. However, in order to properly control or adjust the secondary separation apparatus 412, it is important to obtain accurate testing information of the various particles that are actually separated during secondary separation operation. On the other hand, as previously noted, the available prior art particle analysis systems are typically used for particle size and size distribution analyses, and in some limited cases, particle shape analysis. Therefore, there is a need to develop methods and systems that may be used to determine the density, or specific gravity of individual particles within a particulate material sample so that the efficiency and performance of a separation system can be accurately monitored.

In studying the above-described problem, the inventor has developed various novel methods and systems for determining the specific gravity of individual particles in a particulate material sample by utilizing the particle size analysis apparatuses that are commonly available in the marketplace. In one aspect, the inventor has determined that the specific gravity of individual particles contained within a mixture of particles of different material types may be ascertained by manipulating the motion of the particles within a fluid medium having a known viscosity, observing and gathering data on the manipulated particles using a known particle size analysis apparatus, and, based on the gathered data, calculating the specific gravity of the various observed particles using the principles of Stokes' Law. Accordingly, once a determination has been made regarding the range of particle specific gravity and particle size, the operational proficiency of a separator systems can be thoroughly assessed, and adjustments or corrections made as noted above. The following discussion is directed to various illustrative embodiments of the present disclosure that may be used to analyze a particulate material sample containing a mixture of different particle types based on a Stokes' Law analysis of individual particles.

Accordingly to Stokes' Law, the drag force on a spherical particle passing through a continuous fluid medium is defined as follows:

$$F_d = 6\pi\mu R\upsilon \qquad \text{(Eq. 1)}$$

where: $F_d$=the frictional (drag) force on a particle;
$\mu$=the dynamic viscosity of the fluid medium;
R=the radius of the particle; and
$\upsilon$=the velocity of the particle.

One special case of particle movement through a fluid is based on the terminal (constant) velocity of the particle, that is, when the drag force $F_d$ on the particle is balanced by the gravitational and buoyancy forces acting on the particle, such that the particle is not accelerating as it moves through the fluid. Using this special terminal velocity case, a theoretical equivalent spherical size, or "Stokes' diameter," of a particle can be calculated by observing the terminal (or settling) velocity of the particle as it falls through the fluid. For example, referring to FIG. 7, when a spherically shaped particle 710 falls through a fluid medium (represented by fluid flow lines 711 in FIG. 7), a force $F_g$ is acting on the particle 710 due to the difference between the weight of the particle 710 and its buoyancy in the fluid 711, both of which are caused by gravity. The force $F_g$ is given by the following:

$$F_g = (\rho_p - \rho_f) g 4/3 \pi R^3 \qquad \text{(Eq. 2)}$$

where: $\rho_p$=the mass density of the sphere;
$\rho_f$=the mass density of the fluid;
g=the gravitational acceleration constant; and
R=the radius of the sphere.

As noted above, at the constant terminal (or settling) velocity of the spherical particle 710 in the fluid medium 711, the frictional force $F_d$ on the particle 710 is balanced by the force $F_g$. Therefore, equating the force $F_d$ and the force $F_g$, the terminal velocity is given as follows:

$$v_s = \frac{2}{9} \frac{(\rho_p - \rho_f)}{\mu} g R^2 \qquad \text{(Eq. 3)}$$

where: $\upsilon_s$=terminal (settling) velocity of the sphere.

Based on Equation 3 above, if the terminal (settling) velocity $v_s$, the particle density $\rho_p$, fluid density $\rho_f$, and the fluid viscosity $\mu$ are all known values, then an equivalent spherical radius R of the particle may be calculated. Generally, this technique in determining particle size is viable only when the particle mixture is substantially homogeneous—i.e., when all particles are composed of the same material, and the density (i.e., specific gravity $\rho_p$) of that material is also known. On the other hand, in a mixture that contains a variety of particles that are made up of many different material types, an equivalent spherical particle radius cannot be determined with any degree of certainty, since the density, or specific gravity, of any given individual particle is not known. Therefore, this approach for determining particle size is not typically used when the material of the particles is either mixed or unknown.

The inventor has developed methods and systems for determining the mass density (and therefore, the specific gravity) of individual particles contained within a mixture of particles of different material types based on the Stokes' Law principles outlined above, as will hereinafter be described in detail below.

Figure 5A:
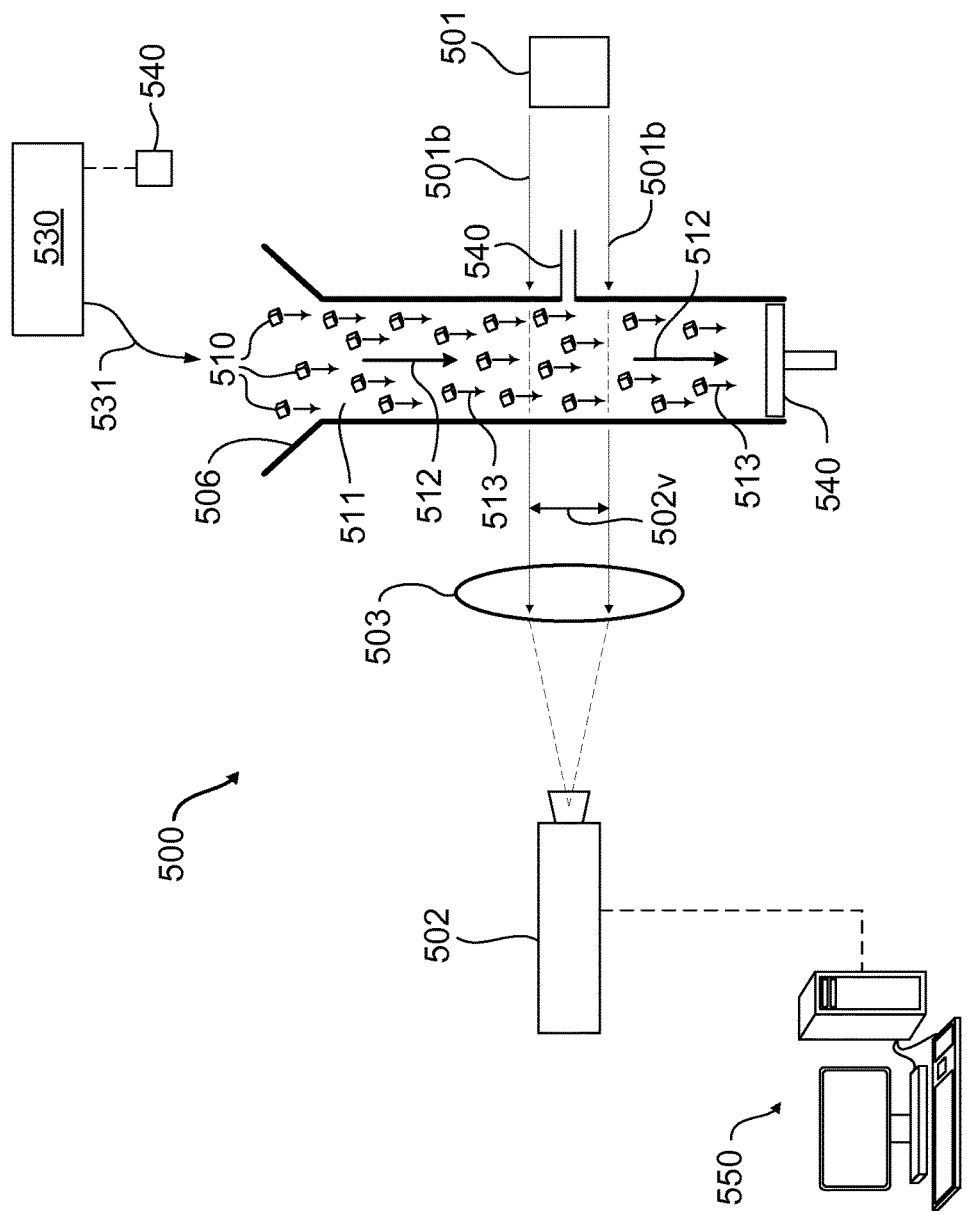
FIGS. 5A-5E are schematic illustrations of various exemplary embodiments of an illustrative particle analysis apparatus disclosed herein.

FIG. 5A schematically depicts a particle analysis apparatus 500 that may be used in conjunction with the methods and systems disclosed herein, and which may be substantially based on a commonly available prior art particle size analysis apparatus, such as, for example, the digital optical imaging apparatus 300 shown in FIG. 3 and described above. As shown in FIG. 5A, the particle analysis apparatus 500 includes a digital camera 502, an optical magnification device 503, a light source 501, and sample delivery means 530 for delivering a particulate material sample 531 containing a plurality of particles 510 to a sample cell 506. Depending on the overall operational requirements of the apparatus 500, sample delivery means 530 may include any one of several sample delivery apparatuses well known in the art. For example, in certain illustrative embodiments, sample delivery means 530 may include a pumping apparatus for pumping the particulate material sample 531 to the sample cell 506, such as a centrifugal pump, a positive displacement pump, and the like. In other embodiments, sample delivery means 530 may include a tank apparatus for facilitating a gravity feed of the sample 531 to the sample cell 506. It should be appreciated by those ordinary skill in the art after a complete reading of the present disclosure that other sample delivery means 530 may also be employed.

The sample cell 506 may be used to direct the plurality of particles 510 of the particulate material sample 531 through a field of view 502v of the digital camera 502. Furthermore, the various illustrated elements of the apparatus 500 may be arranged in substantially similar fashion to the prior art digital optical imaging apparatus shown in FIG. 3 and described above. For example, in some exemplary embodiments, the light source 501 may be operated so that a light beam 501b from the light source 501 passes through the sample cell 506 and illuminates the particles 510 that are passing through the field of view 502v of the digital camera 502 so that digital images can be captured by the camera 502. Furthermore, the optical magnification device 503, such as a lens system and the like, may be used to magnify and focus the digital camera 502 on the particles 510 as they pass through the sample cell 506.

Depending on the design parameters of the apparatus 500, the light source 501 may be, for example, a strobe light, such as an LED strobe light and the like, which may be operable to flash at a frequency that is in the range of approximately 20-50 Hz (flashes per second) so as to enable the digital camera 502 to gather the requisite amount of digital imaging data while a given particle is within the field of view 502v. In at least one embodiment the strobe light source 501 may be operate to flash at approximately 30 Hz During operation of the particle analysis apparatus 500, a fluid medium 511 may be used to dilute the particulate material sample 531 containing the particles 510 so that the particles 510 are substantially dispersed and separated, as previously described. In some embodiments, the particulate material sample 531 may be diluted with the fluid medium 511 prior to the sample 531 being delivered by sample delivery means 530 to the sample cell 506. In other exemplary embodiments, dilution of the particulate material sample 531 with the fluid medium 511 may occur downstream of sample delivery means 530, e.g., in a sample diluting system (not shown) between sample delivery means 530 and the sample cell 506.

Depending on the overall requirements of the particle analysis that is being performed by the apparatus 500, the particulate material sample 531 may be diluted by the fluid medium 511 so that the particles 510 are dispersed/separated within the fluid medium 511 by a distance that ranges from approximately 10-25% of the field of view of the digital camera 502. Such particle dispersion/separation enables each particle 510 to be individually viewed and photographed by the digital camera 502 as the particle 510 passes through the field of view 502v, thereby substantially avoiding image interference from nearby and/or adjacent particles. In certain embodiments, the particle analysis apparatus 500 may be operated so that the fluid medium 511—which may be, for example, a substantially incompressible liquid, such as water, oil, alcohol and the like—is used to actively carry the dispersed/separated particles 510 through the sample cell 506, as indicated in FIG. 5A by the fluid medium directional flow arrows 512. In other embodiments, the fluid medium 511 may initially be substantially static within the sample cell 506—i.e., not flowing—such that the particles 510 are freely falling through the sample cell 506, also as shown by particle directional flow arrows 513.

Unlike the prior art digital optical imaging apparatus 300 described above, the particle analysis apparatus 500 of FIG. 5A may additionally include fluid manipulation means 540 for manipulating the movement of the fluid medium 511 within the sample cell 506. Based on the previously described principles of Stokes' Law, the manipulated fluid medium 511 may in turn influence the movement of the particles 510 as they pass through the sample cell 506, and in particular, while the particles 510 are within and/or passing through the field of view 502v of the digital camera 502. For example, when the particles 510 to be measured are in and/or passing through the field of view 502v, fluid manipulation means 540 may be actuated so as to manipulate the movement of the fluid medium 511 by a known amount (e.g., distance, speed, and/or direction), thereby also influencing the movement of the particles 510. For example, the movement of the particle 510 may be influenced by changing the velocities of the various particles, moving the various particles in different directions, and/or along different paths than the particle direction 513 shown in FIG. 5A, and the like. Digital optical images of the particles 510 may then be obtained using the digital camera 502 as the movement of the particles 510 is influenced, i.e., altered, by actuation of fluid manipulation means 540. The data associated with the digital optical images relative to the altered velocity of the particles 510 may then be analyzed with the data processing apparatus 550, and thereafter used to calculate the specific gravity of the particles 510 based on the principles of Stokes' Law, as will be described in greater detail below.

In certain illustrative embodiments, fluid manipulation means 540 may be, for example, a movable piston device 540p (see, FIGS. 5B and 5E) that is operatively coupled to the sample cell 506 in such a manner so as to be slidably movable inside of the sample cell 506 in a plunger-like fashion. The movable piston device 540p may thereby be used to manipulate the movement of the fluid medium 511, and consequently, influence the movement of the particles 510. Furthermore, in at least some exemplary embodiments, the movable piston device 540p may also be used to oscillate the fluid medium 511 (see, FIG. 5E), as will be further described below. In other embodiments, fluid manipulation means 540 may be, for example, a nozzle or jet 540n (see, FIG. 5C) disposed in one or more sidewalls of the sample cell 506, wherein the nozzle 540n may be positioned substantially within the field of view 502v. In further illustrative embodiments, fluid manipulation means 540 may be a flow control system 540c (see, FIG. 5D) that is operatively coupled to sample delivery means 530. In still other embodiments, fluid manipulation means 540 may include one or more of the movable piston device 540p, the nozzle 540n, and the flow control system 540c. Operation and function of various fluid manipulation means 540 will be discussed in additional detail in conjunction with FIGS. 5B-5E below.

Figure 5B:
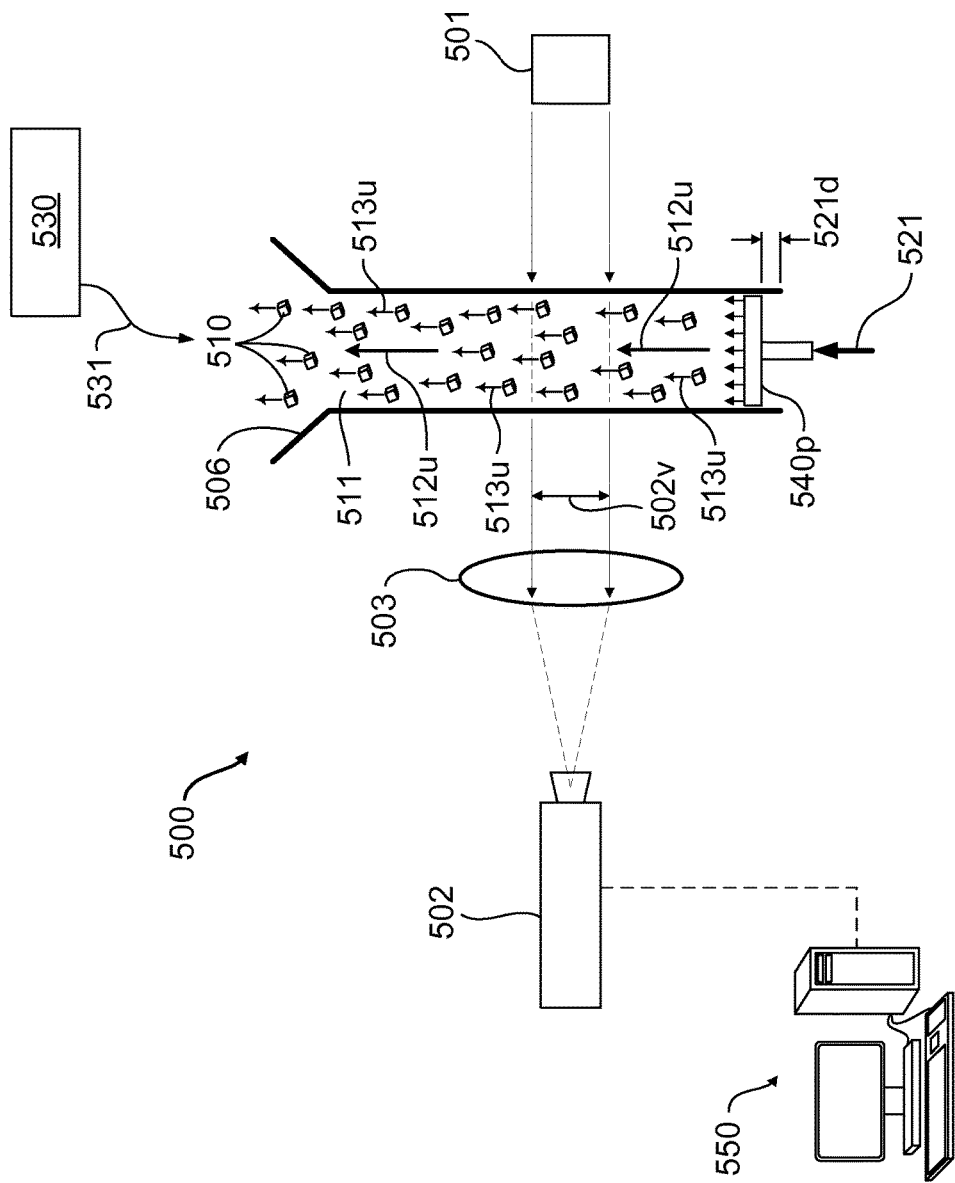

FIG. 5B schematically depicts an illustrative embodiment of the particle analysis apparatus 500 wherein fluid manipulation means 540 is a movable piston device 540p that is positioned proximate one end of the sample cell 506, such as at the bottom end of the sample cell 506 as shown in FIG. 5A. In the depicted example, the movable piston device 540p is adapted to be moved upward, i.e., in the direction 512u that is substantially parallel to but opposite of the direction 512 that the fluid medium 511 is flowing and/or the direction 513 that the particles 510 are moving as they flow with or fall through the fluid medium 511 (see, FIG. 5A).

In those embodiments wherein the fluid medium 511 is a substantially incompressible liquid (e.g., water, oil, alcohol, and the like), fluid manipulation means 540, such as the movable piston device 540p of FIG. 5B, may be actuated to operate in a plunger-like fashion. For example, the movable piston device 540p may be actuated by applying a force 521 that moves the movable piston device 540p at a known velocity and/or over a known displacement distance 521d. Due to the incompressible nature of the fluid medium 511, the movable piston device 540p will push on and move the fluid medium 511 in the direction of the force 521. Furthermore, when the force 521 that is used to move the movable piston device 540p is in the opposite direction of the original fluid medium flow direction 512 and/or the original particle flow direction 513 (see, FIG. 5A), the fluid medium 511 will also be moved in an opposite—e.g., upward—direction 512u, as shown in FIG. 5B. In accordance with the principles of Stokes' Law, the drag force imposed on the particles 510 by the fluid medium 511 moving in the upward direction 512u will influence the movement of the particles 510, thus causing the particles 510 to slow down, come to a stop, and/or reverse direction, such that the particles 510 are moved in an upward direction 513u, as indicated in FIG. 5B.

In certain embodiments, the digital camera 502 may be used to capture digital optical image data of the relative motion of the particles 510 as fluid manipulation means 540, e.g., the movable piston device 540p, is being actuated to manipulate the movement of the fluid medium 511 and influence particle movement. The data associated with the digital optical images may then be analyzed using a data processing apparatus 500 to determine the velocity of the particles 510 as their motion is being manipulated by fluid manipulation means 540. Thereafter, since the velocity vector and specific gravity of the fluid medium 511 are known, and the velocity vectors, and the sizes of the various individual particles 510 can be determined based on the processed digital optical image data, the specific gravities of the various individual particles 510 may be determined based on the principles of Stokes' Law, as will be described in further detail below.

Figure 5C:
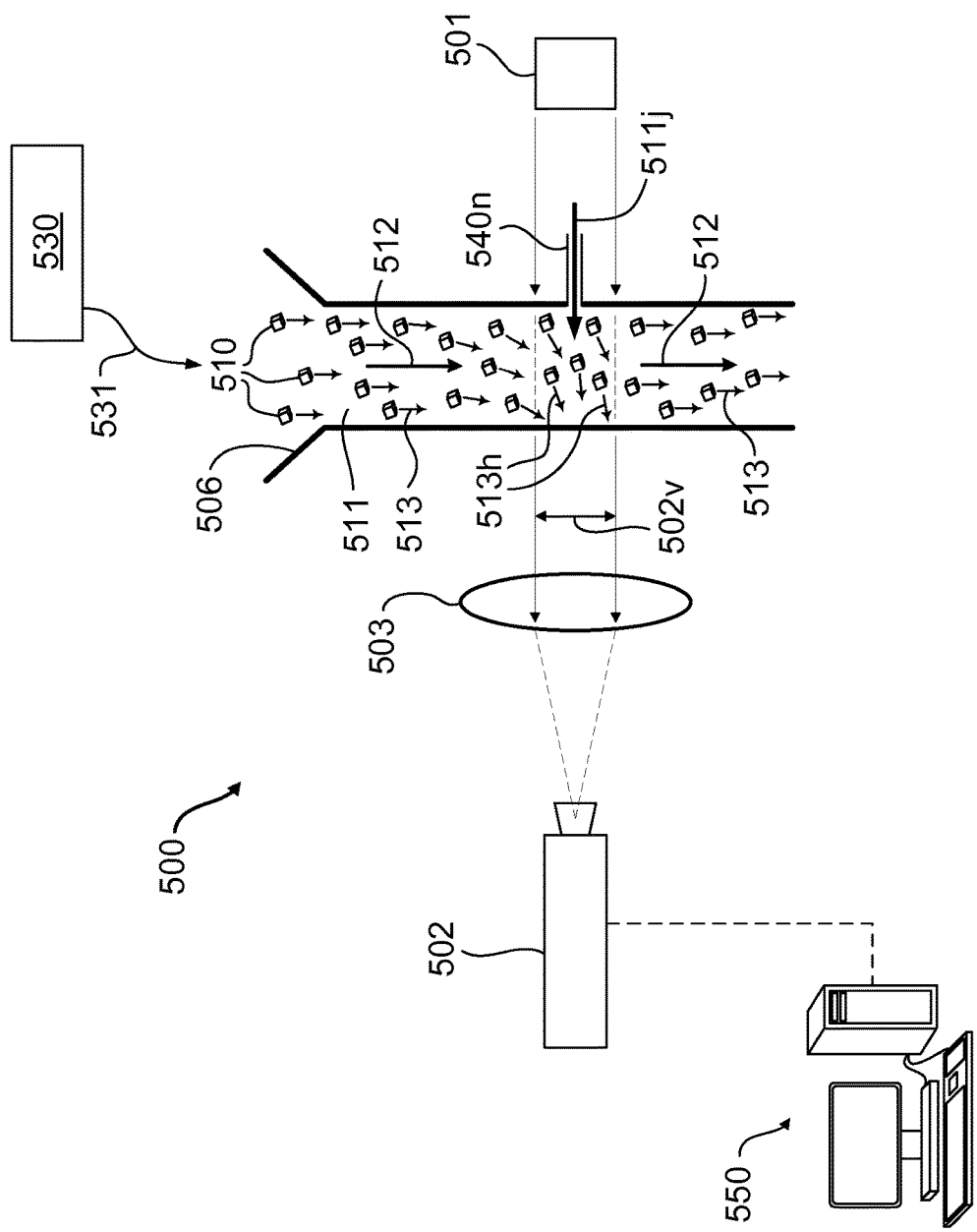

FIG. 5C schematically illustrates another embodiment of the particle analysis apparatus 500 of the present disclosure, wherein fluid manipulation means 540 may be, for example, a nozzle or jet 540n that is disposed in one or more sidewalls of the sample cell 506, which may be used to introduce an additional jet flow 511j into the flow medium 511. In some embodiments, the nozzle 540n may be positioned in the sample cell 506 so that it is located substantially within the field of view 502v. Furthermore, the direction of the jet flow 511j may be substantially orthogonal to—that is, in a substantially lateral direction relative to—the fluid medium flow direction 512 and/or the particle flow direction 513, although it should be appreciated that the nozzle 540n and jet flow 511j may be configured at substantially any angle relative to the nominal flow direction 512 (see, FIG. 5A) of the fluid medium 511. In this way, the jet flow 511j may be used to cause individual particles 510 to move in a non-vertical direction 513h, e.g., in a somewhat lateral or even near-horizontal path, at least during the time the particles 510 are passing through the field of view 502v, as shown in FIG. 5C. As the movement of individual particles 510 is being manipulated, by the jet flow 511j passing through the nozzle 540n, digital optical images of the particles may be obtain using the digital camera 502, and the data associated with the digital optical images may be analyzed in the manner previously described so as to determine the velocity of the particles 510 relative to the fluid medium 511.

In certain exemplary embodiments, the fluid used to create the jet flow 511j may be substantially the same fluid medium 511, such as a substantially incompressible liquid and the like. Furthermore, in at least some embodiments, the jet flow 511j may contain solids particles of a known size and/or know material type (i.e., a known specific gravity), which may thus permit a comparative velocity and drag force assessment relative to the unknown particles 510 flowing through the sample cell 506, based on the principles of Stokes' Law.

Figure 5D:
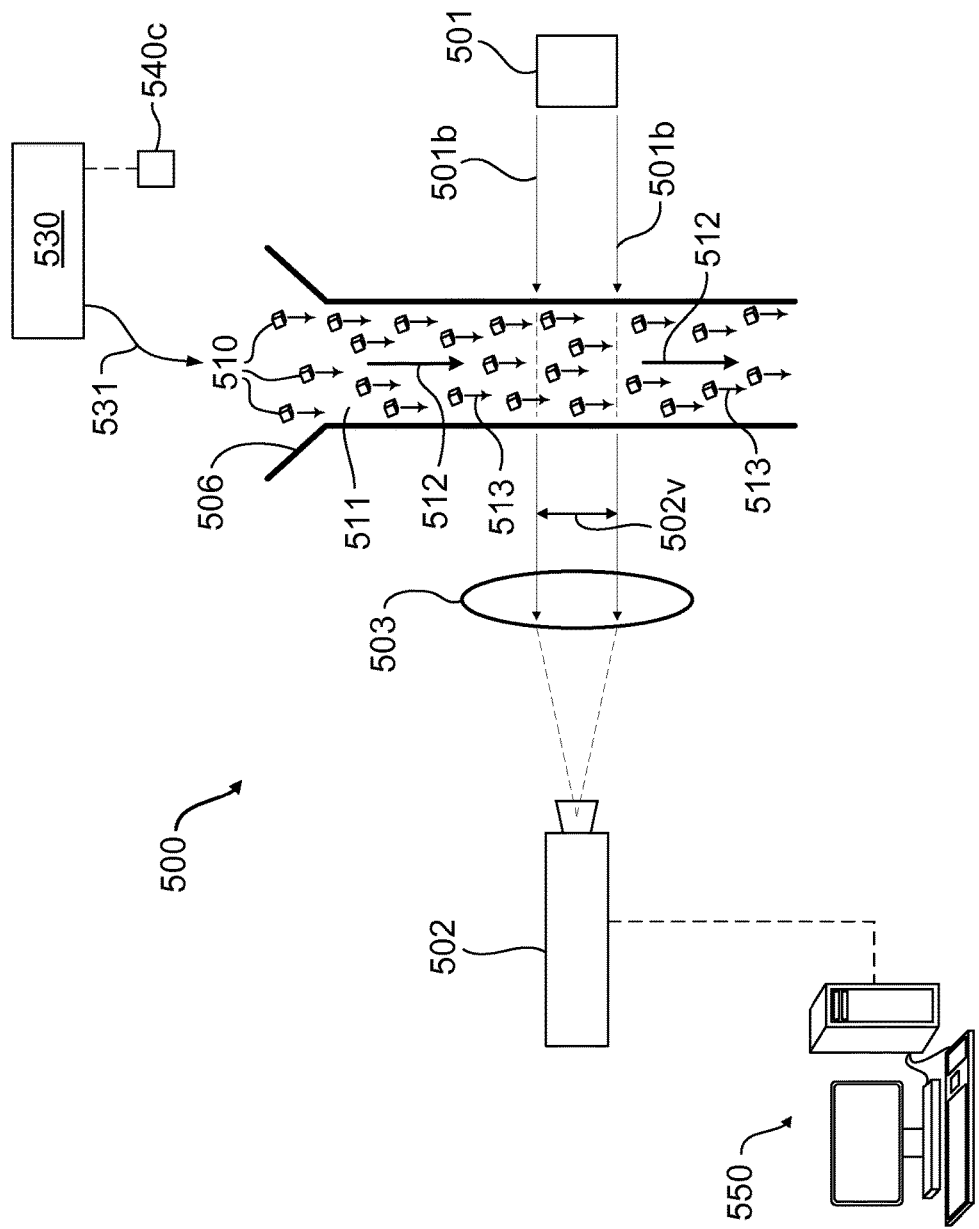

FIG. 5D schematically depicts yet another exemplary embodiment of the particle analysis apparatus 500 of the present disclosure, wherein fluid manipulation means 540 may include a flow control system 540c that is operatively coupled to sample delivery means 530. In some embodiments, the flow control system 540c may be operable to control and/or adjust a flow rate of the particulate material sample 531 (e.g., the mixture of particles 510 and fluid medium 511) delivered to the sample cell 506 by sample delivery means using any one of a variety of different control measures. For example, the flow control system 540c may include, among other things, one or more control valves (not shown), which may be adapted to control one or both of the flow rate of the fluid medium 511 and the volume of particles 510 being delivered to and/or from sample delivery means 530. Furthermore, in those illustrative embodiments wherein sample delivery means 530 includes, for example, a pump, the flow control system 540c may also include an apparatus and/or system for controlling the flow rate of the pump (not shown), such as a variable speed motor drive with electronic drive controller, and the like.

In operation, the flow control system 540c may be operated to adjust the flow rate of the fluid medium 511 that is being delivered to the sample cell 506 by sample delivery means 530. For example, the flow control system 540c may be operated to adjust the flow rate, i.e., the velocity, of the fluid medium 511, i.e., along the flow path 512, from a first known flow rate (or velocity) to a second known flow rate (or velocity). Particles 510 that are within and/or passing through the field of view 502v during this controlled flow rate change may be observed, and digital optical image data related to any changes in movement of the particles 510 (e.g., particle velocities) along their flow paths 513 may be obtained with the digital camera 502. Thereafter, the data obtained in this way from the particles 510 during this controlled flow rate change may then be evaluated using Stokes' Law (as described below) so as to determine the specific gravities of the particles 510.

It should be understood that the flow control system 540c may be operated in such a way as to either increase or decrease the flow rate (velocity) of the fluid medium 511 between two known flow rates (velocities). Furthermore, it should be appreciated that the flow control system may also be operated so as to completely interrupt, or stop, the flow of the fluid medium 511. In such an operational case, one of the two known flow rates (velocities) of the fluid medium 511 would therefore be substantially zero.

Following is an exemplary calculation methodology based on Stokes' Law that may be used for determining the specific gravity of the various solids particles that are present in a diluted particulate material sample and which have been manipulated in one or more of the ways described above and illustrated in FIGS. 5A-5D.

Figure 7:
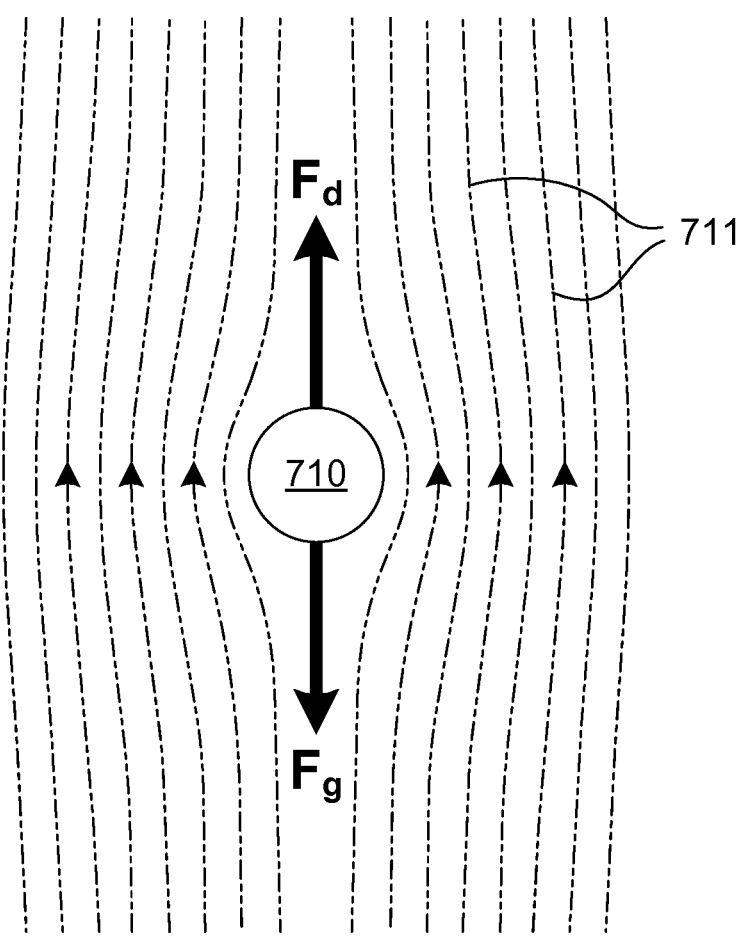
FIG. 7 schematically depicts the drag force and gravitational force on a particle falling through a fluid medium.

As discussed with respect to FIG. 7 above, Equation 3 is often used to evaluate the equivalent spherical size of particles that are settling freely through a stationary fluid under the influence of gravity. However, the inventor has determined that the formula of Equation 3 is equally valid in those cases when the surrounding fluid, e.g. the fluid medium 511, and the particles, e.g. the particles 510, are both moving, provided that the velocity vectors of the particles 510 (as measured by the particle analysis apparatus 500) and the velocity vector of the surrounding fluid medium 511 (due to the controlled operation of the various elements of the apparatus 500 that are used to manipulate the fluid medium 511) are known. Furthermore, it should be appreciated by those of ordinary skill in the art that the velocity of individual particles and the velocity of the surrounding fluid should both be characterized in vector notation, since the force of gravity—which influences the movement of both the fluid and the particles—is also a vector that is oriented in a vertically downward direction. Therefore, since the values of all variables other than the mass density (and hence, specific gravity) of the solid particle in question are known, the mass density of the particle in question can be determined by algebraic manipulation of Equation 3, as shown below.

As a first step, the settling velocity $v_s$ is replaced by the difference between the vertical component of the velocity $v_p$ of the specific particle in question and the vertical component of the velocity $v_f$ of the surrounding fluid medium, both of which may be known based upon operation of a suitable particle analysis apparatus, such as the particle analysis apparatus 500 described herein. Furthermore, as noted above, vector notation is used to reflect that the vector component of these velocities that is used for the analysis is oriented in the vertical direction. Using the following algebraic manipulations, Equation 3 may then be rearranged so as to isolate the only unknown term in the equation—i.e., the mass density of the particle:

$$\vec{v_s} = \frac{2}{9}\frac{(\rho_p - \rho_f)}{\mu}gR^2 = (\vec{v_p} - \vec{v_f}) \quad \text{(Eq. 3a)}$$

$$2(\rho_p - \rho_f)gR^2 = 9\mu(\vec{v_p} - \vec{v_f}) \quad \text{(Eq. 3b)}$$

$$(\rho_p - \rho_f) = \frac{9\mu(\vec{v_p} - \vec{v_f})}{2gR^2} \quad \text{(Eq. 3c)}$$

$$\rho_p = \frac{9\mu(\vec{v_p} - \vec{v_f})}{2gR^2} + \rho_f \quad \text{(Eq. 3d)}$$

where: $\rho_p$=the mass density of the particle;
$\vec{v_p}$=the vertical component of the velocity of the particle;
$\rho_f$=the mass density of the fluid medium;
$\vec{v_f}$=the vertical component of the velocity of the fluid medium;
$\mu$=the viscosity of the fluid medium;
g=the gravitational acceleration constant; and
R=the equivalent spherical radius of the particle.

Thereafter, the specific gravity of the particle in question may be calculated by dividing both sides of Equation 3d by the mass density of water:

$$SG_p = \frac{\rho_p}{\rho_w} = \left[\frac{9\mu(\vec{v_p} - \vec{v_f})}{2gR^2} + \rho_f\right]\frac{1}{\rho_w} \quad \text{(Eq. 4)}$$

where: $SG_p$=the specific gravity of the particle; and
$\rho_w$=the mass density of water.

Figure 5E:
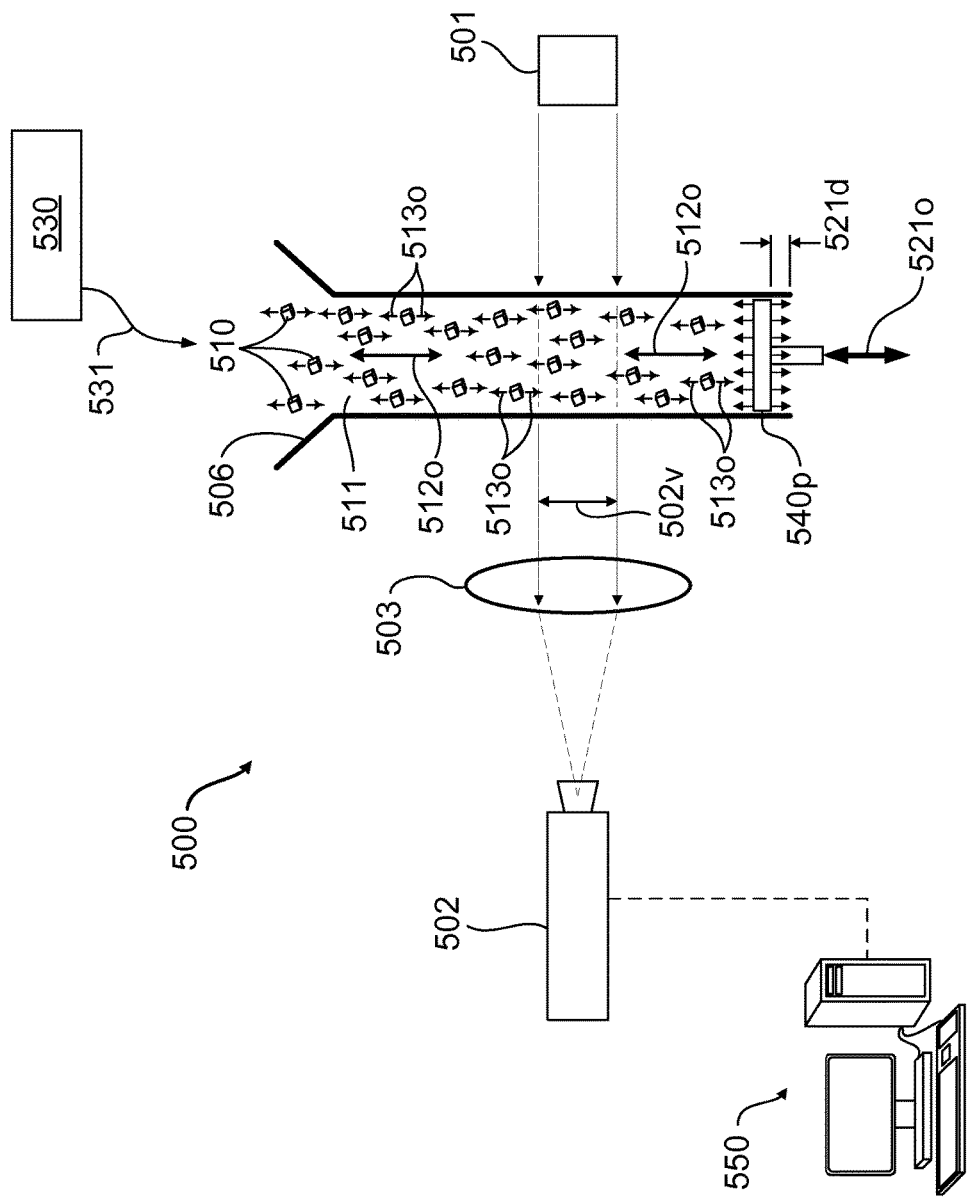

FIG. 5E schematically depicts the exemplary particle analysis apparatus 500 shown in FIG. 5B, wherein the apparatus 500 may be operated in accordance with yet another illustrative method so as to determine the specific gravity of individual particles 510 flowing through the sample cell 506. As depicted in FIG. 5E, the particle analysis apparatus 500 is configured in substantially the same manner as shown in FIG. 5B. However, rather than actuating the movable piston device 540p to move in a single direction—i.e., upward, or opposite to, the particle direction 513, as shown in FIG. 5A)—the movable piston device 540p may be oscillated up and down by a distance 521d, as indicated by the excitation force arrow 5210 in FIG. 5E. In certain embodiments, oscillating distance 521d may be on the order of approximately 0.05-0.50 mm, whereas in at least one embodiment the oscillating distance 521d is about 0.10 mm. The oscillating motion of the movable piston device 540p will thereby cause the fluid medium 511 to also oscillate up and down, as indicated by fluid medium directional motion arrows 512o. Furthermore, as defined by Stokes' Law, the drag force effects between the fluid medium 511 and the particles 510 will also act to manipulate the motion of the particles 510, thereby also imparting an up and down oscillating motion on the particles 510, as indicated by the particle directional motion arrows 513o.

Due to the substantially incompressible nature of the fluid medium 511 (which may be, for example a liquid such as water, oil, alcohol, and the like), the oscillation frequency of the fluid medium 511 will be substantially the same as the oscillation frequency of the movable piston device 540p. However, due to the inertia of the particles 510, and/or their momentum as they fall or flow through the sample cell 506, there will be a delay in the drag force effects of the fluid medium 511 on the particles 510, thus resulting in a phase shift between the frequency at which the movable piston device 540p and the fluid medium 511 are oscillating and the frequency at which the particles 510 are oscillating. This delay in the drag force effects is due at least in part to the fact that Stokes' Law requires a certain amount of time for a given particle to reach terminal velocity in a fluid, which depends on the physical properties of both the fluid and the particle. However, when the particles 510 are manipulated by oscillating the fluid medium there is insufficient time for the resulting velocity of a particle to reach its maximum. Thus, the "jigging" action of the oscillating movable piston device 540p tends to maximize the momentum effect on the particles 510. The resulting phase shift can therefore provide a strong indicator of the specific gravity of the particle, since the size of the particle is known.

During oscillation of the movable piston device 540p, digital optical image data may be obtained of the particles 510 while they are within the field of view 502v of the digital camera 502. Furthermore, during the period of each piston stroke oscillation, the light 501, e.g., an LED strobe light and the like, may be flashed on the order of 10-50 times so that sufficient image data of the particles 510 may be obtained throughout the oscillation. Accordingly, in certain embodiments, the frequency at which the movable piston device 540*p* (and consequently, the fluid medium 511) are oscillated may be carefully coordinated with the flashing frequency of the strobe light 501 so as to substantially ensure that an adequate number of digital optical images are obtained so as to ascertain the oscillation frequency of the particles 510. The image data may then be analyzed using a data processing apparatus 550, such as a computer that utilizes appropriately designed data analysis software, and a determination of the phase shift between the oscillation frequency of the fluid medium 511 and the particles 511 may be made therefrom. Thereafter, the mass density (i.e., the specific gravity) of the measured particles may be calculated using the principles of Stokes' Law, will be further described below.

As noted above, the present disclosure contemplates that any one of the particle analysis apparatuses 500 disclosed herein may be configured in such a way that fluid manipulation means 540 includes a combination of one or more of the various devices and systems described above and illustrated in FIGS. 5A-5E. For example, in certain exemplary embodiments, fluid manipulation means 540 may include a movable piston device 540*p* as shown FIGS. 5B and 5E in combination with the flow control system 540*c* shown in FIG. 5D. In some embodiments of a particle analysis apparatus 500 that is configured in this fashion, the flow control system 540*c* may be operated so as to completely interrupt, i.e., stop, delivery of the particulate material sample 531 (e.g., the mixture of the fluid medium 511 and the particles 510) from sample delivery means 530. Thereafter, the movable piston device 540*p* may be actuated so as to move the fluid medium 511 upward along the path 512*u* (see, FIG. 5B) and/or up and down along the path 512*o* (see, FIG. 5E) at a known constant velocity or displacement 521*d*, during which time digital optical image date may be obtained on the particles 510 within the field of view 502*v* of the digital camera 502, and thereafter analyzed using the data processing apparatus 550. Of course, it should be appreciated by those of ordinary skill after a complete reading of the present disclosure that the above-noted combination of flow control system 540*c* and movable piston device 540*p* is exemplary only, as other combinations that include any or all of the system 540*c*, device 540*p*, and nozzle 540*n* are well within the scope and spirit of the presently disclosed subject matter.

Following is one exemplary approach based on the previously-described Stokes' Law calculation methodologies that may be used for determining the specific gravity of the various solids particles that are present in a diluted particulate material sample which have been oscillated as described above and illustrated in FIG. 5E.

Setting Equation 1 (for drag) equal to Equation 2 (for momentum) results in Stokes' law as is generally used to describe the terminal (settling) velocity of a particle falling under its own weight due to gravity within a viscous fluid. However, the momentum equation (Eq. 2) can also be seen as a specific case of a more familiar form of the equation F=ma:

$$F_g = (\rho_p - \rho_f) g 4/3 \pi R^3 \quad \text{(Eq. 2)}$$

More specifically, it should be understood that the specific value of the gravitational constant g is used in place of the more general acceleration term a. Furthermore the mass density difference multiplied by the particle volume:

$$(\rho_p - \rho_f) \times 4/3 \pi R^3 \quad \text{(Eq. 2a)}$$

should be understood as a specific case wherein an "equivalent mass" of the particle is used in place of the more general mass term m. Therefore, when the various particles, such as the particles 510, are being oscillated by the surrounding fluid, such as the fluid medium 511, the downward force of gravity is no longer the only acceleration force acting on the system. In such cases, the momentum equation can thus expanded to include the vector sum of all of the accelerations acting on the particles—i.e., the accelerations induced by manipulation of the fluid medium, and the acceleration of gravity.

In contrast, the mathematical description of the drag force (Eq. 1) acting on the particles does not change, other than acknowledging the directional aspects of the force. Drag on the particles can therefore be expected to remain oriented in substantial opposition to the velocity vector of the fluid, which thus defines the drag force direction by adding a negative sign to the fluid velocity direction. Therefore, when the directional characteristics of the system, i.e., of the particles and fluids, are addressed by incorporating vector notation into the Stokes' Law equations as set forth above, substantially most, if not all, cases of controlled fluid manipulation and particle movement can be readily analyzed, regardless of system complexity.

It should be understood that, as one step of the illustrative methods disclosed herein, the sizes of the particles 510 present in and/or flowing through the field of view 502*v* of the digital camera 502 may be determined in a manner known to those skilled in the art. For example, using the particle analysis apparatus 500 shown in FIGS. 5A-5E, particle sizes may be determined by obtaining digital optical image data of the particles 510. Thereafter, the digital image data obtained by the digital camera 502 may be transmitted to an image processing system, such as the data processing apparatus 550 shown in FIGS. 5A-5E, that uses a data analysis program and the like, and the processed image data may then be used to calculate the size of individual particles 510 in the manner described with respect to, for example, the prior art apparatus 300 described above. Once an individual particle size has been calculated, a Stokes' Law analysis may then be performed in one or more of the manners described above so as to obtain the density (specific gravity) of the particle.

Furthermore, as may be appreciated by one of ordinary skill having the full benefit of the present disclosure, the size and specific gravity of a given particle may be performed simultaneously, e.g., based on the same digital optical image data that is gathered on the particles as they pass through the field of view 502*v* of the digital camera 502, based upon any of the various embodiments illustrated in FIGS. 5A-5E and described above. However, it should also be appreciated that a plurality of particle size analysis machines may be employed to perform each of the various different types of particle analyses described herein, such as size determination, specific gravity assessment, etc. Moreover, in certain illustrative embodiments, the plurality of machines used to perform these various analyses may each be the same type of particle analysis machine, such as the particle analysis apparatus 500 of FIGS. 5A-5E that utilizes a digital optical imaging system to obtain particle data.

Figure 6:
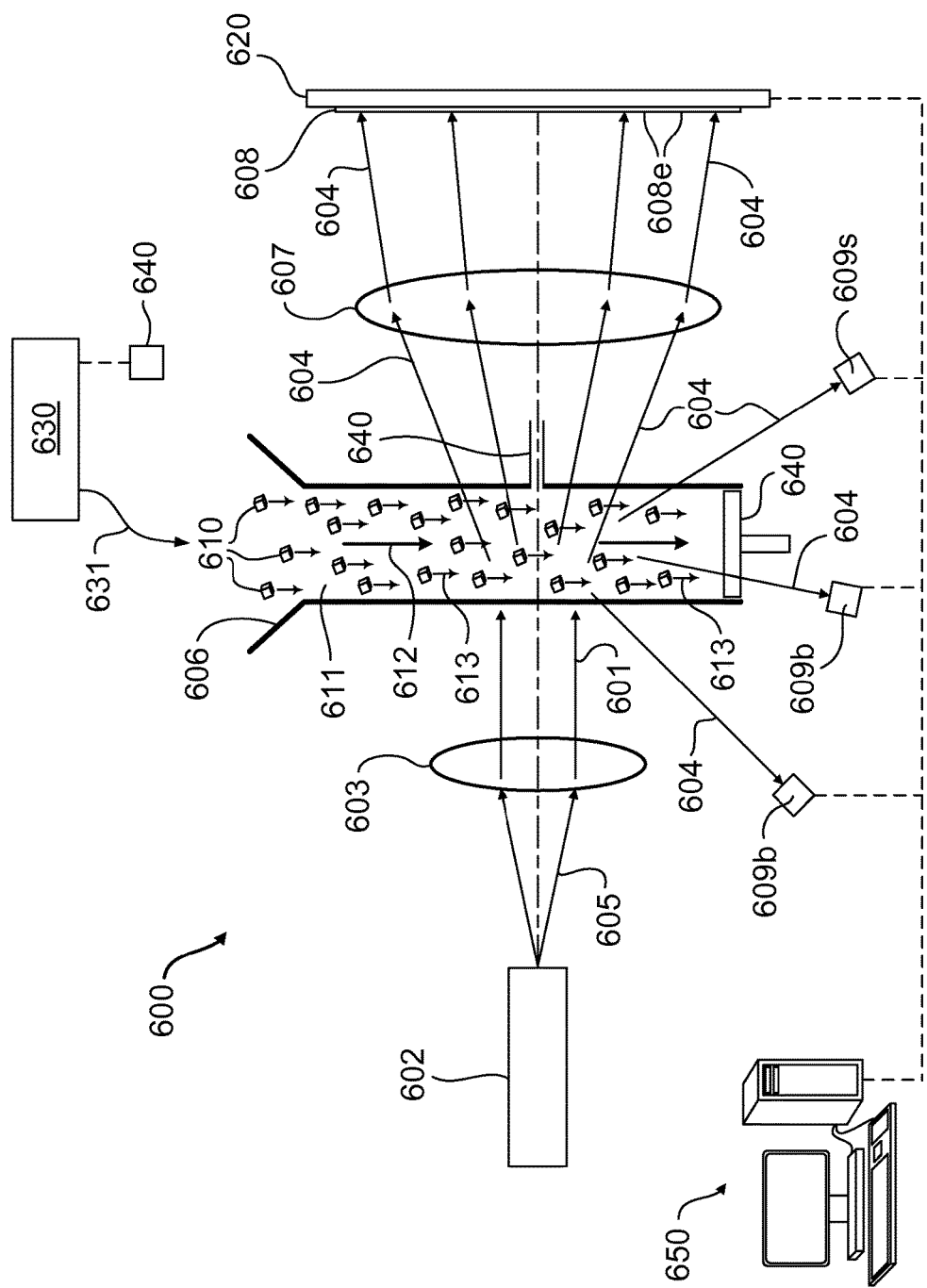
FIG. 6 schematically depicts another illustrative embodiment of a particle analysis apparatus in accordance with the presently disclosed subject matter.

On the other hand, in certain other exemplary embodiments, the plurality of machines used to analyze the various aspects of the measured particles may be different types of particle analysis machines. For example, a particle analysis machine that is substantially based on the prior art digital optical imaging apparatus 300 of FIG. 3 above may be used to perform certain specific analyses on the particles, whereas a particle analysis machine that is substantially based on the prior art laser diffraction apparatus 200 of FIG. 2 may be used to perform other analyses on the same particles. FIG. 6, which schematically depicts an illustrative particle analysis apparatus 600 that is based in part on the prior art laser diffraction apparatus 300, will hereinafter be described briefly below.

As shown in FIG. 6, the particle analysis apparatus 600 may include sample delivery means 630 that is used to deliver a particulate material sample 631 containing a plurality of particles 610 diluted by a fluid medium 611 to a sample cell 606. The apparatus 600 may also include a laser light source 602 and a collimating lens 603, which may be used to facilitate acquisition of particle data, as previously described with respect to the laser diffraction apparatus 200 above. In some embodiments, the particulate material sample 631 (i.e., the mixture of the particles 610 and the fluid medium 611) may flow through the sample cell 606 along the fluid medium flow path 612. Additionally, as with the illustrative embodiments illustrated in FIGS. 5A-5E and described above, the particles 610 typically move through the sample cell 606 along the particle flow path 613. Furthermore, depending on the specific analysis requirements, the particles 610 may either be carried through the sample cell 606 by a flowing fluid medium 611, or they may freely fall through a substantially static (i.e., non-flowing) fluid medium 611.

Light 605 from the laser light source 602 passes through and is focused by the collimating lens 603 into a parallel laser beam 601. The laser beam 601 is used to irradiate the particles 610 as they pass through the sample cell 606, and the particles 610 diffract and/or scatter the laser beam 601, thereby forming a spatial light intensity distribution pattern as previously described. See, e.g., the prior art laser diffraction apparatus 200 shown in FIG. 2 and described above. The particle analysis apparatus 600 may also include a lens 607 that is used to converge the forward diffracted/scattered light 604 onto a detection plane 620, which is disposed at a focal distance position from the lens 607. A ring detector 608 formed from a plurality of light sensor elements 608e having ring-shaped light receiving surfaces of different radii are arranged concentrically on the detection plane 620. See, e.g., FIG. 2 above. In some embodiment, the particle analysis apparatus 600 may also include diffracted/scattered light sensors 609s and 609b for detecting sideward and backward diffracted/scattered light, respectively.

As with the particle analysis apparatus 500 shown in FIG. 5A above, the particle analysis apparatus 600 may similarly include fluid manipulation means 640 for manipulating the movement of, or oscillating the particles 610 as they pass through the sample cell 606. For example, in some embodiments, fluid manipulation means 640 may be a movable piston device that is positioned and actuated in a similar manner to the previously described movable piston device 540p shown in FIGS. 5B and 5E. In other embodiments, fluid manipulation means 640 may be a nozzle or jet that may be positioned and actuated in similar fashion to the nozzle 540n of the apparatus 500 shown FIG. 5C and described above. In certain other exemplary embodiments, fluid manipulation means 640 may be a flow control system that is operatively coupled to sample delivery means 530, which may be configured and operated similar to the flow control system 540c as shown in FIG. 5D, as set forth above.

It should be appreciated by those of ordinary skill after a complete reading of the present disclosure that the illustrative particle analysis apparatus 600 depicted in FIG. 6 may be used in a similar fashion to the apparatus 500 shown in FIGS. 5A-5E so as to determine both the size and specific gravity of the particles 610 as they flow with or fall through the fluid medium 611. Furthermore, it should also be understood that, irrespective of which of the two exemplary particle analysis apparatuses 500, 600 disclosed herein might be used to determine the size and specific gravity of the solids particles contained in a given particulate material sample, the testing data gathered and analyzed by either apparatus may be used to further assess the operational proficiency of a given particle separation system, such as the separation system 408 shown in FIG. 4 above. Based on that assessment, the operational parameters of the particle separation system may be adjusted or controlled so as to obtain the desired machine performance.

In another aspect of the present disclosure, the inventor has determined that the digital optical image data obtained by, for example, the particle analysis apparatus 500 of FIGS. 5A-5E above, may also be used to ascertain the specific material composition of individual particles. More specifically, the digital optical image data may be used to determine various mineralogical properties of the particles 510, such as color, refractive index, birefringence, and the like. For example, in at least some embodiments, the digital optical image information of the red-green-blue (RGB) color spectra that is emitted by the particles 510 may be obtained using an appropriately designed and operated digital camera 502. The digital optical image data representing the RGB color spectra data of individually analyzed particles can then be comparatively assessed relative to the RGB color spectra of known material samples. In other embodiments, digital optical image information on the refractive index or birefringence of the particles 510 may be obtained, and similar comparative assessments based known material samples may also be performed. Such comparative analyses may therefore enable a direct determination—based on optical characteristics—of the various mineralogical properties of the particles 510, including the specific material compositions of the individual particles contained within particulate material sample for which such data is available.

It should be appreciated by those of ordinary skill after a complete reading of the present disclosure that the principles describe herein are not limited to particle separation and particle analysis in oil and gas applications, such as the exemplary mud circulation and recover system 400 illustrated in FIG. 4 and described above. Instead, the methods and systems described herein may be used in any application wherein a mixture of solids particles having different sizes and specific gravities must be separated and/or analyzed. For example, in almost all mining operations, the ores extracted from a mine often contain significant amounts of undesirable solids materials (gangue) and may be very closely intermixed together with the valuable minerals. During mineral processing, the ore is typically finely crushed in a grinding mill, such as a ball mill or SAG mill and the like, after which the valuable mineral must be separated from the remaining material of the crushed mixture.

In the mining industry, various different types of separation may be performed so as to extract the valuable solids particles from the crushed ore mixture, including sizing, gravity concentration, electrostatic separation, magnetic separation, and the like. Depending on the type, or types, of separation processes used, the tailings—i.e., the mixture of waste materials left over after the process of separating the valuable fraction from the uneconomic fraction (gangue) of the ore—may be tested to determine the operational performance of the separation processes, and to ensure that inadvertent quantities of valuable minerals are not carried over with the tailings. It should be appreciated that the various particle analysis methods and systems described above may readily be used in such mining applications to analyze the performance of the ore separation systems used in those applications.

As a result, the subject matter of the present disclosure provides details of various methods and the systems that may be used to determine at least some properties of solids particles, including at least size, specific gravity, and mineralogy.

The particular embodiments disclosed above are illustrative only, as the invention may be modified and practiced in different but equivalent manners apparent to those skilled in the art having the benefit of the teachings herein. For example, the method steps set forth above may be performed in a different order. Furthermore, no limitations are intended to the details of construction or design herein shown. It is therefore evident that the particular embodiments disclosed above may be altered or modified and all such variations are considered within the scope and spirit of the invention. Accordingly, the protection sought herein is as set forth in the claims below.

What is claimed:

1. A system, comprising:
   a particulate material sample comprising a fluid medium and a plurality of particles dispersed in said fluid medium;
   a particle analysis apparatus comprising a sample cell and sample delivery means for delivering said particulate material sample to said sample cell, wherein said particle analysis apparatus is adapted to obtain particle information on at least one particle in said particulate material sample while said at least one particle is in said sample cell;
   fluid manipulation means for manipulating movement of said fluid medium while said particle analysis apparatus is obtaining said particle information on said at least one particle; and
   a data processing apparatus that is adapted to analyze a relationship between a velocity of said manipulated fluid medium and a velocity of said at least one particle and to determine a specific gravity of said at least one particle based on said obtained particle information.

2. The system of claim 1, wherein said fluid medium comprises an incompressible fluid.

3. The system of claim 1, wherein said particle information comprises at least one of a size and a velocity of said at least one particle.

4. The system of claim 1, wherein said particle information comprises a velocity of said fluid medium.

5. The system of claim 1, wherein said fluid manipulation means is adapted to change a velocity of said fluid medium.

6. The system of claim 1, wherein said fluid manipulation means is adapted to oscillate said fluid medium.

7. The system of claim 1, wherein said data processing apparatus is further adapted to determine said specific gravity of said at least one particle by analyzing momentum of and drag forces acting on said at least one particle.

8. The system of claim 1, wherein said particle analysis apparatus is one of a laser diffraction apparatus and a digital optical imaging apparatus.

9. The system of claim 1, wherein said sample delivery means is adapted to flow at least a portion of said particulate material sample to said sample cell prior to actuating said fluid manipulation means to manipulate movement of said fluid medium.

10. The system of claim 1, wherein said fluid manipulation means comprises a movable piston device that is operatively coupled to said sample cell.

11. The system of claim 1, wherein said fluid manipulation means comprises a flow control system that is operatively coupled to said sample delivery means.

12. A method, comprising:
    delivering a particulate material sample to a sample cell of a particle analysis apparatus, said particulate material sample comprising a fluid medium and a plurality of particles dispersed in said fluid medium, at least some of said plurality of particles having different specific gravities;
    obtaining particle information on said particulate material sample with said particle analysis apparatus while said plurality of particles are in said sample cell;
    analyzing said particle information with a data processing apparatus;
    determining a first specific gravity of a first particle of said plurality of particles from said analyzed particle information; and
    determining a second specific gravity of a second particle of said plurality of particles from said analyzed particle information, wherein said second specific gravity is different from said first specific gravity.

13. The method of claim 12, further comprising determining a specific gravity of each of said plurality of particles from said analyzed particle information.

14. The method of claim 12, further comprising manipulating a movement of at least said first and second particles while obtaining said particle information.

15. The method of claim 14, wherein manipulating said movement of at least said first and second particles comprises changing a velocity of at least said first and second particles.

16. The method of claim 14, wherein manipulating said movement of at least said first and second particles comprises oscillating said fluid medium at a first frequency.

17. The method of claim 16, wherein oscillating said fluid medium at said first frequency comprises oscillating said first particle at a second frequency and oscillating said second particle at a third frequency, said second and third frequencies being different than said first frequency.

18. The method of claim 12, wherein determining said first and second specific gravities comprises determining a first velocity of said first particle, a second velocity of said second particle, and a fluid velocity of said fluid medium from said analyzed particle information.

19. The method of claim 12, wherein said first and second specific gravities of said respective first and second particles are determined by analyzing momentum of and drag forces acting on said first and second particles.

20. The method of claim 12, wherein obtaining said particle information on said particulate material sample comprises irradiating said plurality of particles with a laser beam, diffracting or scattering light from said laser beam with said plurality of particles, and detecting said diffracted light or said scattered light with said particle analysis apparatus.

21. The method of claim 12, wherein obtaining said particle information on said particulate material sample comprises obtaining digital optical image data with said particle analysis apparatus.

22. The method of claim 21, wherein obtaining said digital optical image data comprises obtaining data on mineralogical properties of said particulate material sample.

23. The method of claim 22, wherein said data obtained on said mineralogical properties of said particulate matter comprises data on at least one of an RGB color spectra, refractive index, and birefringence of at least said first and second particles.

24. The method of claim 23, wherein determining said first and second specific gravities comprises performing a comparative analysis of at least one of said RGB color spectra, refractive index, and birefringence of said first and second particles relative to at least one of a corresponding RGB color spectra, refractive index, and birefringence of known material samples having known specific gravity values.

25. A system, comprising:
a particulate material sample comprising a fluid medium and a plurality of particles dispersed in said fluid medium;
a particle analysis apparatus comprising a sample cell and sample delivery means for delivering said particulate material sample to said sample cell, wherein said particle analysis apparatus is adapted to obtain particle information on at least one particle in said particulate material sample while said at least one particle is in said sample cell;
fluid manipulation means for manipulating movement of said fluid medium while said particle analysis apparatus is obtaining said particle information on said at least one particle; and
a data processing apparatus that is adapted to determine a specific gravity of said at least one particle based on said obtained particle information by analyzing momentum of and drag forces acting on said at least one particle.

* * * * *